(12) United States Patent
Hayashizaki et al.

(10) Patent No.: US 8,097,414 B2
(45) Date of Patent: Jan. 17, 2012

(54) METHOD FOR DETECTING AND AMPLIFYING NUCLEIC ACID

(75) Inventors: Yoshihide Hayashizaki, Tsukuba (JP); Yasumasa Mitani, Fukuyama (JP); Yuki Kawai, Yokohama (JP)

(73) Assignees: K. K. DNAFORM, Kanagawa (JP); Riken, Saltama (JP)

( * ) Notice: Subject to any disclaimer, the term of this patent is extended or adjusted under 35 U.S.C. 154(b) by 516 days.

(21) Appl. No.: 12/094,896

(22) PCT Filed: Nov. 21, 2006

(86) PCT No.: PCT/JP2006/323213
§ 371 (c)(1),
(2), (4) Date: Aug. 14, 2008

(87) PCT Pub. No.: WO2007/060949
PCT Pub. Date: May 31, 2007

(65) Prior Publication Data
US 2009/0042197 A1   Feb. 12, 2009

(30) Foreign Application Priority Data
Nov. 25, 2005  (JP) ................................. 2005-340685

(51) Int. Cl.
*C12P 19/34* (2006.01)
(52) U.S. Cl. ....................................... 435/6.11; 435/6.12
(58) Field of Classification Search .................. None
See application file for complete search history.

(56) References Cited

U.S. PATENT DOCUMENTS

| | | | |
|---|---|---|---|
| 6,455,256 B1 * | 9/2002 | Engel | 435/6.13 |
| 2002/0102660 A1 * | 8/2002 | Nakayama et al. | 435/91.2 |
| 2004/0023207 A1 * | 2/2004 | Polansky | 435/5 |
| 2007/0190531 A1 * | 8/2007 | Mitani et al. | 435/6 |

FOREIGN PATENT DOCUMENTS

| | | |
|---|---|---|
| EP | 937780 | 12/1998 |
| EP | 1321532 | 12/2002 |
| JP | 4-349900 | 12/1992 |
| JP | 2001-352982 | 12/2001 |
| JP | 2003-159056 | 6/2003 |
| JP | 2005-192554 | 8/2004 |
| WO | WO 2003/054209 | 7/2003 |
| WO | WO 2005063977 A1 * | 7/2005 |

OTHER PUBLICATIONS

International Preliminary Report on Patentability for PCT/JP2006/323213, dated May 27, 2008.*

(Continued)

*Primary Examiner* — Samuel Woolwine
(74) *Attorney, Agent, or Firm* — Alston & Bird LLP

(57) ABSTRACT

Problem to be solved There is provided a method for detecting and/or amplifying a nucleic acid contained in a biological sample such as blood or cells conveniently, rapidly, and effectively.
Solution There is provided a method for detecting a nucleic acid contained in a sample, comprising the step of adding at least one substance selected from the group consisting of polyphenols, polyhydric alcohols, sugar acids, sugar alcohols, and hydrophilic biodegradable polymers to a sample, the step of complementarily binding an oligonucleotide complementary to a part of the nucleic acid sequence of a nucleic acid to be detected to a part of the nucleic acid sequence, and the step of detecting the nucleic acid to be detected.

11 Claims, 15 Drawing Sheets

OTHER PUBLICATIONS

Tichopad et al. Model of inhibition of *Thermus aquaticus* polymerase and Moloney murine leukemia virus reverse transcriptase by tea polyphenols (+)-catechin and (−)-epigallocatechin-3-gallate. Journal of Ethnopharmacology 99:221-7, publicly available online Apr. 9, 2005.*

Jean et al. Detection of hepatitis A virus by the nucleic acid sequence-based amplification technique and comparison with reverse transcription-PCR. Applied and Environmental Microbiology 67(12):5593-5600 (Dec. 2001).*

Koonjul et al. Inclusion of polyvinylpyrrolidone in the polymerase chain reaction reverses the inhibitory effects of polyphenolic contamination of RNA. Nucleic Acids Research 27(3):915-916 (1999).*

"Avoiding False Positives in Colony PCR," *BioTechniques*, 1998, pp. 580-582, vol. 24, No. 4.

Al-Soud, W. and Rådström, P., "Effects of Amplification Facilitators on Diagnostic PCR in the Presence of Blood, Feces, and Meat," *Journal of Clinical Microbiology*, Dec. 2000, pp. 4463-4470, vol. 38, No. 12.

\* cited by examiner

TARGET SEQUENCE (UCP1)

ATAATATTAATGTAAATGTATATATTATATATATAAATGTTATAGTAATTATATAA*CTTGGGTAGT*
*GACAAAGTAT*AATTATTAGGTGAAGTATATGCTTTTTTATTAGTGATAATAAATATAT
CCTCTCCCATTATAAAAGTTTGTATTTCTTCTTTTAGAAATTGATTCTTCTGTCATTT
GCACATTTATCTGTATAATTATAACAGGGTATTCCCAGTGGTGGCTAATGAGAGAATT
ATGGGAAAGTATAGAACACTATTCAAATGCAAAGCACTGTATGATTTTATTTAATAGGA
AGACATTTGTGCAGCGATTTCTGATTGACCACAGTTTGATCAAGTGCATTTGTTAATGT
GTTCTACATTTTCAAAAAGGGAAAGGAGAATTTGTTACATTCAGAACTTGCTGCCACTCC
TTTGCTACGTCATAAAGGGTCAGTTGCCCTTGCTCATACTGACCTATTCTTTACCTCTC
TGCTTCTTCTTTGTGCCAGAAGA*GTAGAAATCTGACCCTTTG*GGATACCACCCTCTCC
CCTACTGCTCTCCAACCTGAGGCAAACTTTCTCCTACTTCCCCAGAGCCTGTCAGAAG
TGGTG   (SEQ ID NO: 9)

PRIMERS

UCP1 PF1    CTTGGGTAGTGACAAAGTAT    (SEQ ID NO: 7)
UCP1 PR1    CCAAAGGGTCAGATTTCTAC    (SEQ ID NO: 8)

Figure 2

CYP2C19-2-OP1    CYP2C19-2-TP
5'-TATTAAATGCTTTTAATTTAATAAATTATTGTTTCTCTTAGATATGCAATAATTTCCCACTATCA
3'-ATAATTTACGAAAATTAAATTATTTAATAACAAAGAGAATCTATACGTTATTAAAGGGTGATAGT
                                                              CYP2C19-2-BP

TTGATTATTTCCCGGGAACCCATAACAAATTACTAAAAACCTTGCTTTTATGGAAAGTGATATTTTGGA
AACTAATAAAGGGCCCTTGGGTATTGTTTAATGAATTTTTGGAACGAAAATACCTTTCACTATAAAACCT
        CYP2C19-2 TP           CYP2C19-2-FP

GAAAGTAAAAGAACACCAAGAATCGA-3' (SEQ ID NO: 10)
CTTTCATTTTCTTGTGGTTCTTAGCT-5'
        CYP2C19-2 OP2

CYP2C19-2 FP      5' cctatatatataggAGGTTTTAAGTAATAATTGTTATGGG 3' (SEQ ID NO: 11)
                                      ↓
CYP2C19-2 TP(W)   5' CCCGGGAAATAATG ATAAATTATTGTTTCTCTTAGATA 3' (SEQ ID NO: 12)
                                      ↓
CYP2C19-2 BP      5' TGATAGTGGGAAAATTATTG 3' (SEQ ID NO: 13)

CYP2C19-2 OP1     5' TATTAAATGCTTTTAATT 3' (SEQ ID NO: 14)

CYP2C19-2 OP2     5' TCGATTCTTGGTGTTCTT 3' (SEQ ID NO: 15)

Figure 5

METHOD FOR DETECTING AND AMPLIFYING NUCLEIC ACID

CROSS-REFERENCE TO RELATED APPLICATIONS

This application is the U.S. National Stage of International Application PCT/JP2006/323213, filed Nov. 21, 2006, which claims the benefit under 35 U.S.C. §119(a) of JP 2005-340685, filed Nov. 25, 2005; both of which are hereby incorporated herein in their entirety by reference.

TECHNICAL FIELD

The present invention relates to a method for detection and for amplification reactions for nucleic acid contained in a biological sample.

BACKGROUND ART

Various methods for detecting and amplifying a nucleic acid contained in a biological sample are known. For example, hybridization methods, in which a nucleic acid is detected by the presence or absence of hybridization of a probe and the target nucleic acid, and methods in which a target nucleic acid is amplified by elongating primers.

A cell contains many impurities, such as pigments and proteins, and these impurities inhibit hybridization of a probe or a primer with a target site or in annealing and reactions such as PCR. Therefore, for detection and amplification of a nucleic acid contained in a biological sample, a nucleic acid must be extracted and purified from a biological sample before employing these methods. For extraction and purification of nucleic acid, cells are lysed, and proteins are further removed using phenol, chloroform, or isoamyl alcohol. Alternatively, a method is employed in which proteins are inactivated with a surfactant or a high salt concentration and are degraded with a protease.

For concentration of a nucleic acid or removal of salts, phenol, and the like, ethanol or isopropanol is added to precipitate the nucleic acid. After a nucleic acid is purified by several such procedures including centrifugation steps, hybridization or amplification is performed.

It is known that detection and amplification of nucleic acid extracted from a biological sample such as blood, cells, and feces, and that has been purified, are inhibited by, in particular, impurities contained in the biological sample. It has been confirmed that this inhibitory effect is attenuated by adding bovine serum albumin, single-stranded DNA binding T4 gene 32 protein (gp32), betaine, proteinase inhibitors, and the like (Non-Patent Document 1).

Furthermore, it is known that, as a convenient method for preparing a template for a PCR method, cells are lysed by heating in an alkali and then neutralized to use as a template, or a nucleic acid sample can be obtained by using cells or a tissue mixed with water and heated as a template without being subjected to inhibition in a PCR analysis (Non-Patent Document 1, etc.).

It is known that it is particularly difficult to amplify a nucleic acid having a high GC content by a PCR method and that PCR amplification efficiency can be increased by adding a polyhydric alcohol and/or ammonium sulfate to the PCR reaction mixture in PCR using purified DNA having a high GC content (Patent Document 1).

Furthermore, it is known that, to increase efficiency of the nucleic acid amplification reaction, a biological sample containing the nucleic acid is treated with an acid in any step of nucleic acid extraction to remove substances interfering with nucleic acid amplification, and the obtained nucleic acid extract is used (Patent Document 2).

Patent Document 1: Japanese Patent Laid-Open No. 2001-352982
Patent Document 2: Japanese Patent Laid-Open No. 2003-159056
Non-Patent Document 1: J. Clin. Microbiol. 2000 December; 38(12) 4463-70
Non-Patent Document 2: Bio Techniques, 1998, (4), 580-582

DISCLOSURE OF THE INVENTION

Problems to be Solved by the Invention

In an actual diagnostic setting, it is necessary to detect a target nucleic acid from a small amount of a sample rapidly and reliably. To this end, it is necessary to subject the nucleic acid to extraction and purification as described above. However, not only do these procedures require time and labor, but it may be difficult to remove impurities completely from some biological samples. Furthermore, there is a problem in that quantitative nucleic acid detection may be impossible because the yield of nucleic acids or the degree of removal of impurities may vary depending on the conditions of extraction and purification.

Furthermore, since nucleic acid detection techniques based on nucleic acid amplification enables detection of a trace amount of a nucleic acid, errors due to contamination are more likely to occur with more complicated steps. Therefore, when steps such as nucleic acid extraction and purification are included to remove impurities, there would be a greater chance of contamination.

However, since inhibitory effects of bovine serum albumin and the like investigated in the non-patent documents may not be attenuated depending on the type of polymerase used or a biological sample, bovine serum albumin and the like may not be widely used for amplification and detection of a nucleic acid. In particular, the heme compound contained in blood cells has a potent inhibitory effect in a PCR reaction.

Means for Solving the Problems

Therefore, a method for pretreatment of a biological sample, such as of blood or cells, is desired by which the biological sample can be subjected to detection and/or amplification reactions of nucleic acid conveniently, rapidly, and effectively.

The inventors of the present invention assiduously researched substances that reduce or inhibit actions of impurities inhibiting detection and amplification of a nucleic acid, and they discovered a method by which a nucleic acid can be detected and/or amplified conveniently and rapidly by addition to a biological sample without performing steps of nucleic acid extraction and purification.

The inventors of the present invention found that the efficiency of nucleic acid detection and/or amplification is improved by adding at least one substance selected from the group consisting of polyphenols, polyhydric alcohols, sugar acids, sugar acid salts, sugar alcohols, and hydrophilic biodegradable polymers to a sample.

That is, the present invention relates to a method for detecting and/or amplifying a nucleic acid contained in a sample, comprising steps of: adding at least one substance selected from the group consisting of polyphenols, polyhydric alcohols, sugar acids, sugar alcohols, and hydrophilic biodegradable polymers to the sample; complementarily binding an oligonucleotide that is complementary to a part of the nucleic acid sequence of a nucleic acid to be detected to the above-mentioned part of the above-mentioned nucleic acid sequence; and detecting the nucleic acid to be detected.

A heating step may be further included prior, at the same time as, or subsequent to the above-mentioned step of adding a substance. A step of adding an alkaline solution may be included prior to, at the same time as, or subsequent to the above-mentioned step of adding a substance. Furthermore, both the heating step and the alkali treatment step using an alkaline solution may be included.

Generally, a nucleic acid is extracted from a biological sample and purified inadvance to improve efficiency of nucleic acid detection and/or amplification. In the method of the present invention, however, a nucleic acid can be detected by adding at least one substance selected from the group consisting of polyphenols, polyhydric alcohols, sugar acids, sugar alcohols, and hydrophilic biodegradable polymers directly to a sample, without performing the nucleic acid extraction and purification. The sample can be selected from blood (including whole blood and separated blood cells) or oral mucosal cells.

The step of complementarily binding an oligonucleotide can be performed as a step of hybridizing a probe, and then a nucleic acid to be detected can be detected by a method selected from the group consisting of Southern blot hybridization, Northern blot hybridization, the invader assay method, the PALSAR assay method, the colony hybridization assay method, the LCR assay method and the bDNA assay method.

The step of complementarily binding an oligonucleotide can be performed as a step of annealing a primer. In this case, a step of amplifying a nucleic acid by elongating a nucleic acid strand from the 3' end of the primer may be further included. The step of amplifying a nucleic acid may be performed by an isothermal amplification method. Furthermore, the step of amplifying a nucleic acid may be performed by a method selected from the group consisting of PCR methods, the TMA method, the NASBA method, the LAMP method, the ICAN method, the RCA method, the TRC method, the SDA method, and the MITANI method. In particular, a nucleic acid can be amplified by the LAMP method or the SMAP method (MITANI method).

Examples of polyphenols include catechin, chlorogenic acid, tannic acid, flavonoid, tannin, rutin, quercetin, isoflavone, and anthocyanin and mixtures thereof. Examples of sugar acids and sugar acid salts include pentaric acid, hexaric acid, gluconic acid, hydroxy acid, galacturonic acid, mannuronic acid, and glucaric acid or salts thereof, and mixtures thereof. Examples of sugar alcohols include sorbitol, mannitol, galactitol, xylitol, and mixtures thereof. Examples of hydrophilic biodegradable polymers include polyethylene glycol (PEG), polypropylene glycol, polybutylene glycol, and copolymers thereof, polyalkylene oxide, polyvinylpyrrolidone, polysaccharides, polyacrylamide, polymethacrylamide, polyvinyl alcohols, and mixtures thereof. Examples of polyhydric alcohols include glycerol, ethylene glycol, propylene glycol, butane diol, hexane diol, octane diol, glycerine, sorbitan, trimethylol propane, neopentyl glycol, and mixtures thereof.

Furthermore, the present invention relates to a kit for detecting a nucleic acid, including at least one substance selected from the group consisting of polyphenols, polyhydric alcohols, sugar acids, sugar acid salts, sugar alcohols, and hydrophilic biodegradable polymers as well as a probe.

Furthermore, the present invention relates to a kit for amplifying a nucleic acid, including at least one substance selected from the group consisting of polyphenols, polyhydric alcohols, sugar acids, sugar acid salts, sugar alcohols, and hydrophilic biodegradable polymers, primers, deoxyribonucleotides, and a polymerase. The present invention relates particularly to the above-mentioned kit for the LAMP method or the MITANI method.

Advantages of the Invention

If a sample that has not been subjected to nucleic acid extraction and purification treatments is used, a target nucleic acid can be directly detected and amplified in a rapid and convenient manner. Furthermore, since the method of the present invention is convenient, a target nucleic acid can be accurately detected and/or amplified without increasing chances of contamination.

BEST MODE FOR CARRYING OUT THE INVENTION

In the present invention, a target nucleic acid can be effectively detected and/or amplified, without being adversely affected by inhibitory actions of impurities, by adding one or two or more substances selected from the group consisting of polyphenols, polyhydric alcohols, sugar acids, sugar acid salts, sugar alcohols, and hydrophilic biodegradable polymers to a biological sample. Furthermore, instead of, or in addition to, the treatment with these substances, a target nucleic acid can also be effectively detected and/or amplified by adding a surfactant without being adversely affected by inhibitory actions of impurities.

It appears that a complementary binding of an oligonucleotide having a sequence complementary to a target nucleic acid to the nucleic acid is not subjected to, or becomes less subject to, inhibitory actions of impurities by adding the above-mentioned substances. Therefore, hybridization of a probe with a target nucleic acid or annealing of a primer with a target nucleic acid is smoothly performed. When efficiency of annealing of a primer to a target nucleic acid is increased, efficiency of elongation of a nucleotide strand from the 3' end of the primer is also increased, resulting in improvement of the nucleic acid amplification efficiency.

In addition to the addition of the above-mentioned substances, heat treatment may be performed. Heat treatment can be performed prior to, substantially at the same time as, or subsequent to addition of the above-mentioned substances. The heating temperature can be set at 37° C. or higher, preferably 45° C. or higher, more preferably 55° C. or higher, and even more preferably 80° C. or higher. The heating time is not particularly limited and can be extremely short. For example, heat treatment can be performed for 0.01 seconds or longer or 3 seconds or longer, preferably 1 minute or longer, and even more preferably 3 minutes or longer. For example, heating at 98° C. for 3 minutes can be mentioned as one example of heating conditions, but those skilled in the art can freely set times and temperatures other than these conditions. Furthermore, this heat treatment can be performed as one step of a reaction including heating, such as PCR methods.

Furthermore, alkali treatment may also be performed with the addition of the above-mentioned substances. Alkali treatment can be performed by mixing an alkaline solution in a sample prior to, substantially at the same time as, or subsequent to addition of the above-mentioned substances. Examples of the alkaline solution include, but are not limited to, solutions of alkali metal hydroxides such as, for example, sodium hydroxide solutions and potassium hydroxide solutions. The alkali concentration (concentration of $OH^{-1}$) can be set at 0.1 mM or higher or 1 mM or higher, preferably 10 mM or higher, and more preferably 30 mM or higher. Alternatively, pH can be set at 7 or higher, preferably 8 or higher, and more preferably 9 or higher. The treatment can be performed at an arbitrary alkali concentration or pH as long as the subsequent detection or amplification step is not inhibited (for example, 10 M or lower).

Furthermore, both heat treatment and alkali treatment can be performed. For example, the above-mentioned substances are added to a sample and further mixed with an alkaline solution, and then heat treatment can be performed at 98° C. for 3 minutes.

A probe hybridizable with a part of the sequence of a nucleic acid to be detected or a primer annealed with a part of the sequence of a nucleic acid to be detected can be used as an oligonucleotide. The probe has a sequence complementary to the sequence of a nucleic acid to be detected or to a strand complementary thereto. As long as it is hybridizable with the sequence of a nucleic acid to be detected or to a strand complementary thereto, all the nucleotides of the probe need not be complementary to the sequence of a nucleic acid to be detected or to a strand complementary thereto. Furthermore, as a part thereof, a probe may have a sequence that is not complementary to the sequence of a nucleic acid to be detected or to a strand complementary thereto. Furthermore, a probe may be labeled for detection. For example, a probe may be labeled with a radioactive isotope, a fluorescent substance, an enzyme, any other chemical substance, or the like. A probe can be used in an immobilized form or adsorbed on a solid phase surface or in free form. The immobilized or adsorbed probe can be used, for example, in the form of a DNA chip or a DNA microarray.

A primer has a sequence complementary to the sequence of a nucleic acid to be detected or to a strand complementary thereto and may be used as a primer set comprising two or more primers. As long as it can be annealed to the sequence of a nucleic acid to be detected or to a strand complementary thereto, all the nucleotides of the primer need not be complementary to the sequence of a nucleic acid to be detected or a sequence complementary to a strand complementary thereto. Furthermore, as a part thereof, a primer may have a sequence that is not complementary to the sequence of a nucleic acid to be detected or to a sequence complementary to a strand complementary thereto. Examples of sequences that are not complementary to the sequence of a nucleic acid to be detected or to a strand complementary thereto and comprised as a part of a primer include promoters of RNA polymerases and the like. Furthermore, a primer may be labeled for detection. For example, a primer may be labeled with a radioactive isotope, a fluorescent substance, an enzyme, any other chemical substance, or the like.

The sequence of a nucleic acid to be detected may be a sense nucleotide sequence or an antisense nucleotide sequence, as long as, for example, the gene includes a double-stranded nucleic acid. For example, a sense nucleic acid sequence (i.e., the nucleotide sequence of the gene) can be detected by detecting an antisense nucleic acid sequence complementary thereto. Nucleic acids to be detected are nucleic acids unique to, for example, viruses, bacteria, protozoa, multicellular organisms, plasmids, or organisms having a nucleic acid of a genetic condition or the like such as a mutation in a gene related to predisposition or disposition to a certain disease, and are, in particular, RNA or DNA.

In the present invention, a substance selected from the group consisting of polyphenols, polyhydric alcohols, sugar acids, sugar alcohols, and hydrophilic biodegradable polymers is added to a sample. The amount added varies depending on the type of the added substance and the sample, but is, for example, 0.001 to 100 mM as a final concentration.

Examples of polyphenols to be added include catechin, flavonoids such as flavan, chlorogenic acid, phenolic acids such as tannic acid, ellagic acids, and so forth. Examples thereof include flavonoid, catechin, tannin, rutin, chlorogenic acid, quercetin, isoflavone, anthocyanin, and so forth. Furthermore, one type of polyphenol may be used, or two or more types thereof may be used in combination. Polyphenol is a plant component having two or more phenolic hydroxyl groups within one molecule.

Examples of polyhydric alcohols include aromatic polyhydric alcohols such as those obtained by adding ethylene oxide to bisphenol and aliphatic polyhydric alcohols such as ethylene glycol, propylene glycol, butane diol, hexane diol, octane diol, glycerine, sorbitan, trimethylol propane, and neopentyl glycol. Specific examples thereof include glycerol, sorbitol, xylitol, and so forth. Polyhydric alcohol is an alcohol having two or more hydroxyl groups, and examples thereof include dihydric to hexahydric alcohols.

As sugar acids, pentaric acids, hexaric acids (including gluconic acid), and the like can be used. Examples of sugar acids include α-hydroxy acid, D-galacturonic acid, D-mannuronic acid, D-gluconic acid, and D-glucaric acid. Examples of sugar acid salts include sodium salts of equivalents of these sugar acids. Sugar acid is a generic term of glucaric acids and carboxyl acids.

Examples of sugar alcohols include sugar alcohols such as sorbitol, mannitol, galactitol, and xylitol. Sugar alcohol is a carbohydrate having an alcoholic hydroxyl group.

Examples of hydrophilic biodegradable polymers include polyalkylene glycols (for example, polyethylene glycol [PEG], polypropylene glycol, polybutylene glycol, and polymers thereof), polyalkylene oxides, polyvinylpyrrolidone, polysaccharides, polyacrylamide, polymethacrylamide, polyvinyl alcohols, and derivatives thereof.

As surfactants, any of cationic surfactants, anionic surfactants, ampholytic ion surfactants, and non-ionic surfactants can be used, and either polymers or low molecular weight compounds can be used. Examples of surfactants include pure soap contents, α-sulfofatty acid ester salts, straight alkyl benzenesulfonates, alkyl sulfuric acid ester salts, alkyl ether sulfuric acid ester salts, α-olefin sulfonates, alkyl sulfonates, sucrose fatty acid esters, sorbitan fatty acid esters, polyoxyethylene sorbitan fatty acid esters, polyoxyethylene fatty acid esters, fatty acid alkanol amides, alkyl glucosides, polyoxyethylene alkyl ethers, polyoxyethylene alkylphenyl ethers, alkyl aminofatty acid salts, alkyl betaines, alkyl amine oxides, alkyl trimethyl ammonium salts, and dialkyl dimethyl ammonium salts. Specific examples include N,N-bis(3-D-gluconamidopropyl)cholamide [BIGCHAP], N,N-bis(3-D-gluconamidopropyl)deoxycholamide [Deoxy-BIGCHAP], NIKKOL BL-9EX [polyoxyethylene(9)lauryl ether], octanoyl-N-methylglucamide [MEGA-8], nonanoyl-N-methylglucamide [MEGA-9], decanoyl-N-methylglucamide [MEGA-10], polyoxyethylene(8)octylphenyl ether [Triton X-114], polyoxyethylene(9)octylphenyl ether [NP-40], polyoxyethylene(10)octylphenyl ether [Triton X-100], polyoxyethylene(20)sorbitan monolaurate [Tween 20], polyoxyethylene(20)sorbitan monopalmitate [Tween 40], polyoxyethylene(20)sorbitan monostearate [Tween 60], polyoxyethylene(20)sorbitan monooleate [Tween 80], polyoxyethylene(20)sorbitan trioleate, polyoxyethylene(23)lauryl ether [Brij35], polyoxyethylene(20)cethyl ether [Brij58], n-dodecyl-β-D-maltopyranoside, n-heptyl-β-D-thioglucopyranoside, n-octyl-β-D-glucopyranoside, n-octyl-β-D-thioglucopyranoside, n-nonyl-β-D-thiomaltoside, IGEPAL CA-630, Digitonin, saponin from soybeans, 3-[(3-cholamidopropyl)dimethylammonio]-2-hydroxy-1-propanesulfonate [CHAPSO], 3-[(3-cholamidopropyl)dimethylammonio]-1-propanesulfonate [CHAPS], sodium dodecylsulfate [SDS], lithium dodecyl sulfate [LDS], lithium 3,5-diiodosalicylate, Tris(hydroxymethyl)aminomethane dodecyl sulfate [Tris DS], sodium cholate, N-lauroylsarcosine, sodium N-dodecanoylsalcosinate, cetyldimethylethylammonium bromide, cetyltrimethylammonium bromide [CTAB], cetyltrimethylammonium chloride, guanidine thiocyanate.

Examples of biological samples include, but are not limited to, samples derived from animals, plants, and microorganisms. Examples of samples derived from animals include, but are not limited to, blood (including whole blood and separated blood cells), serum, plasma, cells (including cultured cell systems), tissues, body fluids (ear discharge, nasal discharge, pus, ascites, pleural exudate, bile, cerebrospinal fluid, sputum, etc.), mucosal cells (oral mucosal cells, stomach mucosal cells, respiratory tract mucosal cells, etc.) sweat, amniotic fluid, excretory substances (urine, feces, etc.), scrapings from organs by an endoscope or the like, collected sample solutions, biopsy samples, alveoli wash, and so forth. Examples of samples derived from plants include, but are not limited to, the entire plant body, cultured cells, and organs such as tissues, roots, stems, leaves, flowers, and seeds. Examples of samples derived from microorganisms include microorganism cultures and the like. Furthermore, not only biological samples, but freely selected samples such as seawater and soil can be used.

According to the present invention, efficient detection can be achieved, and detection sensitivity can be improved because inhibition of probe hybridization or primer annealing by impurities can be reduced or inhibited by adding polyphenols, polyhydric alcohols, sugar acids, sugar acid salts, sugar alcohols, or hydrophilic biodegradable polymers, even when impurities are contained in a sample.

Examples of methods in which a nucleic acid is detected using a probe include, but are not limited to, Southern blot hybridization for detecting DNA, Northern blot hybridization for detecting RNA, the invader assay method, the PALSAR method, and the bDNA assay method.

Southern blot hybridization is a method for detecting DNA having a target sequence, and it is generally performed by the following procedures. DNA is digested with restriction enzymes and is separated by agarose electrophoresis. DNA in the agarose gel is denatured into single strands by alkali treatment. Subsequently, DNA fragments are transferred from the electrophoresed gel to a membrane such as a nitrocellulose membrane or a nylon membrane, and DNA having a sequence complementary to a probe labeled with an enzyme or a radioactive isotope is detected by hybridization with the probe.

Northern blot hybridization is a method for detecting RNA having a target sequence, and is generally performed by the following procedures. RNA in the denatured form is separated by agarose electrophoresis. Subsequently, RNA is transferred from the electrophoresed gel to a membrane such as a nitrocellulose membrane or a nylon membrane, and RNA having a sequence complementary to a probe labeled with an enzyme or a radioactive isotope is detected by hybridization with the probe.

The invader method is a method for detecting a single nucleotide polymorphism (SNP) by detection of a fluorescent signal using an enzyme that specifically recognizes a change in the structure of one nucleotide mismatch in a target DNA, and is generally performed by the following procedures.

Three kinds of probes referred to as an allele probe, an invader probe, and a FRET probe are prepared. The allele probe has a sequence specific to a template toward the 3' side and a sequence (flap) unrelated to the template sequence toward the 5' side. The 5' end of the 3' side sequence of the allele probe specific to the template is an SNP site and is designed to be complementary to nucleotides of an allele to be detected. The invader probe is designed to complementarily bind to the 3' side of the template from the SNP site, and a nucleotide corresponding to the SNP site may be an arbitrary nucleotide. The FRET probe has a sequence complementary to the flap on the 3' side and a palindrome sequence for forming a hairpin structure on the 5' side. A fluorescent dye binds to the 5' end of the FRET probe, and a quencher binds in the vicinity thereof.

These three kinds of probes are hybridized with the target DNA, so that an enzyme can cleave it. At this time, when the nucleotide of the allele probe corresponding to the SNP site complementarily binds to the SNP site nucleotide, the 3' end of the invader probe invades the sequence. This structure is recognized by a cleavage enzyme, and the allele probe is cleaved at the flap site to free the flap region. The freed flap binds to the FRET probe. When the flap binds to the FRET probe, this structure is further recognized by the cleavage enzyme, the 5' end of the FRET probe is cleaved, a fluorescent dye quenched by a quencher is freed, and the fluorescence is detected.

In the PALSAR assay method, two kinds of DNA probes comprising three complementary regions prepared beforehand are labeled and allowed to repeat hybridization to form a large DNA aggregation bound and amplified in a beehive-like shape, which serves as a signal. The existence of a gene to be detected can be confirmed by allowing the gene to bind to this signal. Since this method does not require a nucleic acid synthetase in the process of hybridization and can be performed isothermally, it is convenient, and the reaction can be performed in a short time. Both DNA and RNA can be detected with high sensitivity.

The bDNA assay method is a method for detecting a nucleic acid, which is also referred to as the branched strand probe method or the bDNA probe method. A probe and a nucleic acid are hybridized, the hybrid is further hybridized with an amplified molecule referred to as a branched DNA, and a target nucleic acid is detected by detecting it.

Examples of nucleic acid amplification techniques using primers include, but are not limited to, PCR methods, the TMA method, the NASBA method, the LAMP method, the ICAN method, the RCA method, the SDA method, the MITANI method, and so forth. These amplification techniques may further include a step of detecting a target nucleic acid by detecting an amplified nucleic acid. Both amplification methods utilizing cyclic changes of temperature such as PCR and isothermal amplification methods allowing isothermal reactions can be used. Examples of isothermal amplification methods include the TMA method, the NASBA method, the LAMP method, the ICAN method, the RCA method, the SDA method, the TRC method, and the MITANI method.

A PCR method is a technique in which one set of primers complementary to a template DNA are designed, and a region flanked by the primers is amplified by DNA polymerase in a reaction vessel. Various modified PCR methods are available. Various modifications such as the RT-PCR method, in which DNA is synthesized from RNA using a reverse transcriptase before performing PCR and the TaqMan PCR method, in which only a specific allele is amplified using a TaqMan probe, a fluorescent probe for typing SNP, and Taq DNA polymerase, are known to those skilled in the art.

The TMA method is a method for specifically amplifying a target RNA in which a transcript is obtained from a template RNA by an RNA polymerase having an RNase activity using a forward primer having a sequence identical to a target RNA and a reverse primer having a sequence complementary to the target RNA on the 3' side and a promoter sequence that recognizes T7 RNA polymerase on the 5' side, and the obtained transcript is further synthesized using the obtained transcript as a template.

The NASBA method is a method for specifically amplifying a target RNA in which a transcript is obtained from a template RNA by a DNA-dependent RNA polymerase using a forward primer having a sequence identical to a target RNA and a reverse primer having a sequence complementary to the target RNA on the 3' side and a promoter sequence that recognizes T7 RNA polymerase on the 5' side, and a transcript is further synthesized using the obtained transcript as a template.

The LAMP method is a method in which a loop is always formed at the 3' end of a synthesized DNA, primers are annealed within the loop, and specific amplification of the target DNA is performed isothermally.

The ICAM method is a method in which specific amplification of a target DNA is performed isothermally by a strand substitution reaction, a template exchange reaction, and a nick introduction reaction, using a chimeric primer comprising RNA-DNA and DNA polymerase having a strand substitution activity and RNase H.

The SDA method is a method in which a target DNA is amplified by using a DNA strand substituted with a strand synthesized by a strand substitution type DNA polymerase lacking a 5'->3' exonuclease activity by a single-stranded nick generated by a restriction enzyme as a template of the next replication.

The MITANI (SMAP) method is a method developed by the inventors of the present invention, in which a target nucleic acid is continuously synthesized under isothermal conditions using a primer set comprising two kinds of primers and DNA or RNA as a template. The first primer included in the primer set includes, in the 3' end region thereof, a sequence (Ac') hybridizable with a sequence (A) in the 3' end region of a target nucleic acid sequence as well as, on the 5' side of the above-mentioned sequence (Ac'), a sequence (B') hybridizable with a sequence (Bc) complementary to a sequence (B) existing on the 5' side of the above-mentioned sequence (A) in the above-mentioned target nucleic acid sequence. The second primer includes, in the 3' end region thereof, a sequence (Cc') hybridizable with a sequence (C) in the 3' end region of a sequence complementary to the above-mentioned target nucleic acid sequence as well as a loopback sequence (D-Dc') comprising two nucleic acid sequences hybridizable with each other on an identical strand on the 5' side of the above-mentioned sequence (Cc').

These techniques for nucleic acid detection and amplification are known to those skilled in the art, and the present invention can be applied to freely selected reactions, as long as they are detection involving hybridization of a probe and/or amplification reaction involving primer annealing.

Example 1

Effect of Additives in SMAP Method and PCR Method

In this example, oral mucosal cells were used as a biological sample, and a target nucleic acid sequence in the human CYP2D6 gene contained therein was amplified by the SMAP method (MITANI method), or a target nucleic acid sequence in the UCP1 gene was amplified by a PCR method to examine improvement of amplification effects of various additives. Tannic acid was added in the SMAP method, and sodium glucuronate was added in the PCR method.

As primers in the SMAP method, a primer set having the following sequences (2D6*44-F1 and 2D6*44-SR2 [SEQ ID NOS: 1 and 2, respectively]) was used. Furthermore, positions of the primer regions corresponding to a template (SEQ ID NO: 3) are shown in FIG. 1. Unless otherwise specified, primer sequences and the like are written with the left hand side as the 5' side and the right hand side as the 3' side in the present specification.

The forward primer 2D6*44-F1 was designed so that a sequence existing on the 3' side (20mer: the underlined region in the following sequence) should be annealed with the template and elongated, and a sequence existing on the 5' side of the primer 2D6*44-F1 (10mer: other than the underlined region in the following sequence) should be hybridized with a region starting 15 nucleotides downstream of the 3' end nucleotide of the primer 2D6*44-F1 on a strand elongated from the primer 2D6*44-F1. That is, the elongation product of the primer 2D6*44-F1 can form a stem loop structure having a 35mer loop by hybridization within the strand.

The reverse primer 2D6*44-SR2 was designed so that a sequence existing on the 3' side (20mer: the underlined region of the following sequence) should be annealed with the template, and that a sequence existing on the 5' side (16mer: other than the underlined region in the following sequence) should loop back at the 8th nucleotide from the 5' end to form a hairpin structure.

```
FORWARD PRIMER 2D6*44-F1:
CGCTGCACATGGCCTGGGGCCTCCTGCTCA          (SEQ ID NO: 1)

REVERSE PRIMER 2D6*44-SR2:
tttatatatatataaaCCCCTGCACTGTTTCCCAGA    (SEQ ID NO: 2)

LOOP PRIMER 2D6*44-LF4:
ATCCGGATGTAGGATC                        (SEQ ID NO: 4)

2D6*44OF4:
GATGGTGACCACCTCGAC                      (SEQ ID NO: 5)

2D6*44OR4:
TGTACCCTTCCTCCCTCG                      (SEQ ID NO: 6)
```

As primers for the PCR method, a primer set having the following sequences (UCP1 PF1 and UCP1 PR1 [SEQ ID NOS: 7 and 8, respectively]), was used. Furthermore, the positions of the primer regions corresponding to the template (SEQ ID NO: 9) are shown in FIG. 2.

```
UCP1 PF1 CTTGGGTAGTGACAAAGTAT    (SEQ ID NO: 7)

UCP1 PR1 CCAAAGGGTCAGATTTCTAC    (SEQ ID NO: 8)
```

25 µL of a reaction mixture was prepared. The composition of the reaction mixture is as follows. As a sample containing DNA used as a template, oral mucosal cells were used.

TABLE 1

| Compositions of reagents used in SMAP method (final concentration) | |
|---|---|
| Tris-HCl (pH 8.8) | 20 mM |
| KCl | 10 mM |

TABLE 1-continued

Compositions of reagents used in
SMAP method (final concentration)

| | |
|---|---|
| $(NH_4)_2SO_4$ | 10 mM |
| $MgSO_4$ | 8 mM |
| Tween | 0.1% |
| DMSO | 5% |
| dNTP | 1.4 mM |
| SYBR green | Diluted 100,000-fold |
| 2D6*44-F1 and 2D6*44-SR2 | 2.16 μM each |
| 2D6*44-LF4 | 1.08 μM |
| 2D6*44OF4 and 2D6*44OR4 | 0.27 μM each |
| Oral mucosal cells | 1 μL |
| tannic acid | 0.4 mM |
| Bst DNA polymerase | 8 U/μL |
| $H_2O$ | Added to make 25 μL as final volume |

TABLE 2

Compositions of reagents used in
PCR method (final concentration)

| | |
|---|---|
| Tris-HCl (pH 8.8) | 20 mM |
| KCl | 10 mM |
| $(NH_4)_2SO_4$ | 10 mM |
| $MgSO_4$ | 2 mM |
| Triton-X100 | 0.1% |
| dNTP | 0.25 mM |
| SYBR green | Diluted 100,000-fold |
| Primer F | 1 μM |
| Primer R | 1 μM |
| Oral mucosal cells | 1 μL |
| Sodium glucuronate | 0.4 mM |
| Taq DNA polymerase | 0.1 U/μL |
| $H_2O$ | Added to make 10 μL as final volume |

The reaction mixture was reacted by the SMAP method (MITANI method) at 60° C. for 1 hour. Furthermore, the cycle in the PCR method consisted of heating at 95° C. for 5 minutes, followed by 60 cycles of at 95° C. for 30 seconds, at 60° C. for 30 seconds, and at 72° C. for 30 seconds. After amplification, it was confirmed by DNA sequencing that the amplification product was the amplified target sequence.

The amplification curves obtained by the SMAP method and the PCR method using real time PCR MX3000P are shown in FIGS. 3 and 4, respectively. FIG. 3 shows that amplification by the SMAP method was performed more rapidly when tannic acid was added compared to the case in which it was not added. FIG. 4 shows that amplification by the PCR method was performed more rapidly when sodium glucuronate was added. It is thought that addition of tannic acid or sodium glucuronate made the amplification more rapid and improved amplification efficiency because efficiency of annealing the primers to the target nucleic acid was increased compared to the cases in which they were not added.

Example 2

Effect of Additives by SMAP Method

In this example, blood was used as a biological sample, and improvement of effect of amplifying a target nucleic acid sequence (SEQ ID NO: 10) in the human CYP2C19 gene contained therein by the SMAP method (MITANI method) after adding a surfactant in alkali treatment of blood.

As primers for the SMAP method, a primer set having the following sequences (CYP2C19-2 [SEQ ID NOS: 11 to 15]) was used. Furthermore, the positions of the primer regions corresponding to the template are shown in FIG. 5.

The forward primer CYP2C19*2FP was designed so that a sequence existing on the 3' side (25mer: the underlined region in the following sequence) should be annealed with the template, and that a sequence existing on the 5' side (16mer: other than the underlined region in the following sequence) should loop back at the 8th nucleotide from the 5' end to form a hairpin structure.

CYP2C19-2 TP(W) was designed so that a sequence existing on the 3' side (25mer: the underlined region in the following sequence) would be annealed to the template and elongated. The primer CYP2C19-2 TP(W) was designed so that a sequence existing on the 5' side (14mer: other than the underlined region in the following sequence) should be hybridized with a region starting 24 nucleotides downstream of the 3' end nucleotide of the primer CYP2C19-2 TP(W) on the strand elongated from the primer CYP2C19-2 TP(W). That is, the elongation product of the primer CYP2C19-2 TP(W) can form a stem-loop structure having a loop by hybridization within the strand.

```
CYP2C19-2 FP:
                                    (SEQ ID NO: 11)
5'CCTATATATATATAGGAGGTTTTTAAGTAATTTGTTATGGG 3'

CYP2C19-2 TP(W):
                                    (SEQ ID NO: 12)
5'CCCGGGAAATAATCATAAATTATTGTTTTCTCTTAGATA 3'

CYP2C19-2 BP:
                                    (SEQ ID NO: 13)
5'TGATAGTGGGAAAATTATTG3'

CYP2C19-2 OP1:
                                    (SEQ ID NO: 14)
5'TATTAAATGCTTTTAATT3'

CYP2C19-2 OP2:
                                    (SEQ ID NO: 15)
5'TCGATTCTTGGTGTTCTT3'
```

25 μL of a reaction mixture was prepared. The composition of the reaction mixture was as follows. Blood was used as a sample containing DNA used as a template.

TABLE 3

Compositions of reagents used in
SMAP method (final concentration)

| | |
|---|---|
| Tris-HCl (pH 8.8) | 20 mM |
| KCl | 10 mM |
| $(NH4)_2SO_4$ | 10 mM |
| $MgSO_4$ | 8 mM |
| Tween20 | 0.1% |
| DMSO | 5% |
| dNTP | 1.4 mM |
| SYBR green | Diluted 100,000-fold |
| CYP2C19-2 FP and CYP2C19-2 TP(W) | 2.16 μM each |
| CYP2C19-2BP | 1.08 μM |
| CYP2C19-2 OP1 and CYP2C19-2 OP2 | 0.27 μM each |
| Treated blood (containing 14% or no Tween20) | 1 μL |
| Taq DNA polymerase | 0.2 U/μL |
| $H_2O$ | Added to make 25 μL as final volume |

In alkali treatment and heat treatment of the sample in the SMAP method, 5 μL of Tween 20 or 5 μL of distilled water was added to 10 μL of the collected blood and then stirred, 20 μL of NaOH (50 mM) was added to the mixture and then stirred, and the mixture was heated at 98° C. for approximately 3 minutes and then rapidly cooled to 4° C.

The amplification curves obtained by the SMAP method using real time PCR MX3000P are shown in FIG. 6. FIG. 6 shows that amplification by the SMAP method was performed more rapidly when Tween 20 was added compared to the case in which it was not added. It is thought that addition of Tween 20 made the amplification more rapid and improved amplification efficiency because efficiency of annealing the primers with the target nucleic acid was increased compared to the case in which it was not added.

Example 3

Effect of Additive and Heating on Nucleic Acid Amplification by SMAP Method

In this example, human whole blood was used as a biological sample, and a target nucleic acid sequence in the human CYP2D6 gene contained therein was amplified. The same primers as used in Example 1 were used. The reaction conditions and the like were the same as in Example 1.

25 µL of a reaction mixture was prepared. The composition of the reaction mixture was the same as that of the reagents used in the SMAP method of Example 1, except that blood was used as a sample containing DNA used as a template, and chlorogenic acid was used as an additive.

In heat treatment of the sample, 6 µL of EDTA (25 mM) was added to 3 µL of the collected blood, and the mixture was dissolved and homogenized, followed by addition of 1 µL of 5 mM chlorogenic acid. 10 µL of this solution was heated at 98° C. for 3 minutes. After amplification, it was confirmed by DNA sequencing that the amplification product was the amplified target sequence.

The amplification curves obtained by the SMAP method using real time PCR MX3000P are shown in FIG. 7. FIG. 7 shows that amplification by the SMAP method was performed more rapidly when chlorogenic acid was added, and the mixture was heated, compared to the case in which the sample was heated without adding it. It is thought that addition of chlorogenic acid and further heat treatment made the amplification more rapid and improved amplification efficiency because efficiency of annealing the primers with the target nucleic acid was increased compared to the case in which it was not added.

Example 4

Effects of Additives and Alkali Treatment on Nucleic Acid Amplification by SMAP Method and PCR Method In this example, oral mucosal cells or blood was used as a biological sample, and a target nucleic acid sequence in the human CYP2D6 gene contained therein was amplified by the SMAP method (MITANI method), or a target nucleic acid sequence in the UCP1 gene was amplified by a PCR method to examine improvement of amplification effects by various additives and alkali treatment. Chlorogenic acid was added in the SMAP method, and sodium glucuronate was added in the PCR method. The same primers as used in Example 1 were used in both the SMAP method and the PCR method. The reaction conditions and the like were the same as in Example 1.

25 µL of a reaction mixture was prepared. The composition of the reaction mixture was the same as that of the reagents used for the SMAP method and the PCR method in Example 1, except that chlorogenic acid was used as an additive in the SMAP method, and blood was used as a sample and sodium glucuronate was used as an additive in the PCR method.

In the alkali treatment of the sample for the PCR method, scraped oral mucosal cells were dissolved in 10 µL of NaOH (25 mM), followed by addition of 1 µL of 5 mM chlorogenic acid, and the mixture was allowed to stand at room temperature for approximately 15 minutes. Then, 40 µL of 0.1 M Tris-HCl was added for neutralization. In the alkali treatment of the sample for the SMAP method, 3 µL of the collected blood and 6 µL of NaOH (50 mM) were mixed, followed by addition of 1 µL of 5 mM sodium glucuronate, and the mixture was allowed to stand at room temperature for approximately 15 minutes.

After amplification, it was confirmed by DNA sequencing that the amplification product was the amplified target sequence.

The amplification curves obtained by the SMAP method and the PCR method using real time PCR MX3000P are shown in FIGS. 8 and 9, respectively. FIGS. 8 and 9 show that amplification by the SMAP method or the PCR method was performed more rapidly when chlorogenic acid or sodium glucuronate was added before alkali treatment compared to the cases in which each of these was not added before alkali treatment. It is thought that addition of chlorogenic acid or sodium glucuronate and further alkali treatment made the amplification more rapid and improved amplification efficiency because efficiency of annealing the primers with the target nucleic acid was increased compared to the cases in which none of them was added.

Example 5

Effect of Additives and Alkali and Heat Treatment on Nucleic Acid Amplification by SMAP Method and PCR Method In this example, oral mucosal cells or blood was used as a biological sample, and a target nucleic acid sequence in the human CYP2D6 gene contained therein was amplified by the SMAP method (MITANI method), or a target nucleic acid sequence in the UCP1 gene was amplified by a PCR method to examine improvement of amplification effects by various additives, alkali treatment, and heat treatment. Catechin was added in both the SMAP method and the PCR method. The same primers as used in Example 1 were used in both the SMAP method and the PCR method. The reaction conditions and the like were the same as those in Example 1.

25 µL of a reaction mixture was prepared. The composition of the reaction mixture was that of the reagents used in Example 1, except that catechin was used as an additive, and blood was used as a sample in the PCR method.

In the alkali treatment and heat treatment of the sample for the PCR method, scraped oral mucosal cells were dissolved in 10 µL of NaOH (25 mM), followed by addition of 1 µL of 10 mM catechin, and the mixture was heated at 98° C. for approximately 3 minutes. Then, 40 µL of 0.1 M Tris-HCl was added for neutralization.

In the alkali treatment and heat treatment of the sample for the SMAP method, 3 µL of collected blood and 6 µL of NaOH (50 mM) were mixed, followed by addition of 1 µL of 10 mM catechin, and the mixture was heated at 98° C. for approximately 3 minutes.

After amplification, it was confirmed by DNA sequencing that the amplification product was the amplified target sequence.

The amplification curves by the SMAP method and the PCR method using real time PCR MX3000P are shown in FIGS. 10 and 11, respectively. FIGS. 10 and 11 show that amplification by the SMAP method or the PCR method was performed more rapidly when catechin was added before alkali treatment and heat treatment compared to the case in which it was not added before alkali treatment and heat treatment. It is thought that addition of catechin and further alkali and heat treatments made the amplification more rapid and improved amplification efficiency because efficiency of annealing the primers to the target nucleic acid was increased compared to the case in which it was not added.

Example 6

Effect of Additives and Alkali and Heat Treatment on Nucleic Acid Amplification by SMAP Method and PCR Method In this example, oral mucosal cells or blood was used as a biological sample, and a target nucleic acid sequence in the human CYP2D6 gene contained therein was amplified by the SMAP method, or a target nucleic acid sequence in the UCP1 gene was amplified by the PCR method to examine improvement of amplification effects of various additives and alkali treatment. Catechin or polyethylene glycol was added in the SMAP method, and catechin was added in the PCR method. The same primers as used in Example 1 were used in both the SMAP method and the PCR method. The reaction conditions and the like were the same as in those in Example 1, but the experiment was repeated three times for each sample in this example.

25 µL of a reaction mixture was prepared. The composition of the reaction mixture was the same as that of the reagents used in Example 5, except that catechin was used as an additive, and that blood was used as a sample in the PCR method. After amplification, it was confirmed by DNA sequencing that the amplification product was the amplified target sequence.

Amplification curves obtained by the SMAP method and the PCR method using real time PCR MX3000P are shown in FIGS. 12 to 15. FIG. 12 shows a target nucleic acid sequence in the CYP2D6 gene amplified by the SMAP method using oral mucosal cells as a sample after adding catechin. FIG. 13 shows the CYP2D6 gene amplified using blood as a sample after adding polyethylene glycol. FIG. 14 shows the UCP1 gene amplified by the PCR method using blood as a sample after adding catechin. FIG. 15 shows the UCP1 gene amplified by the PCR method using oral mucosal cells as a sample after adding catechin.

FIGS. 12 to 15 show that amplification by the SMAP method and the PCR method was performed more rapidly when catechin or polyethylene glycol was added compared to when they were not added.

BRIEF DESCRIPTION OF THE DRAWINGS

FIG. 2 shows positions of the primers corresponding to the template used in the PCR method.

FIG. 5 shows positions of the primers corresponding to the template used in the SMAP method in Example 2.

SEQUENCE LISTING

Figure 1:
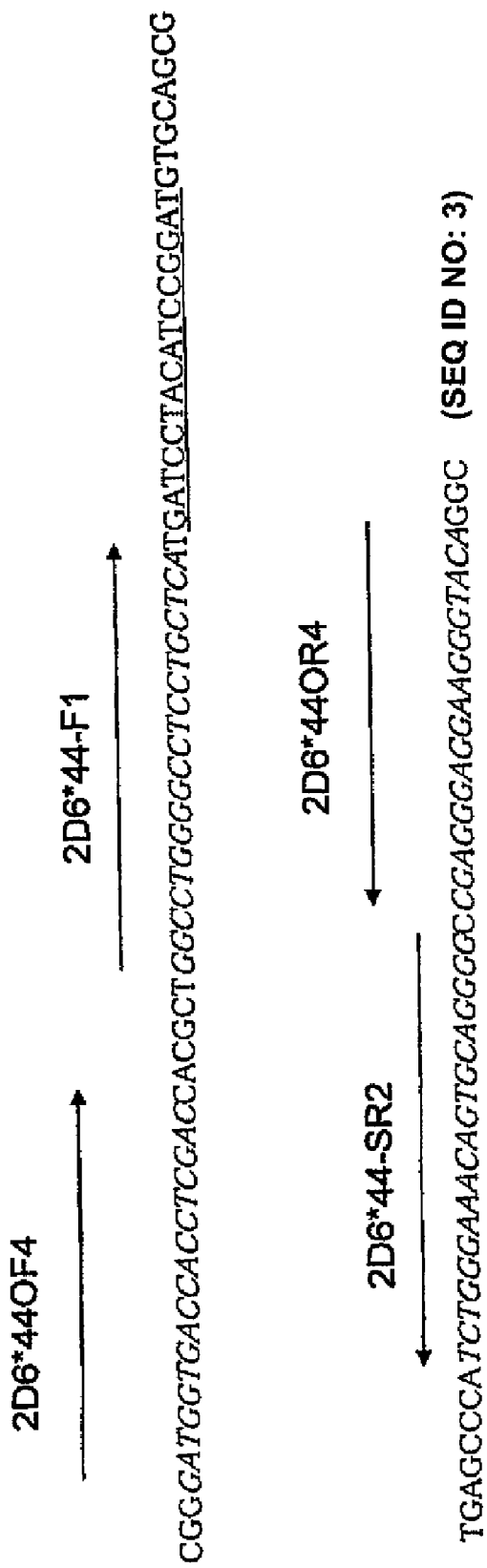
FIG. 1 shows positions of the primers corresponding to the template used in the SMAP method.
Figure 3:
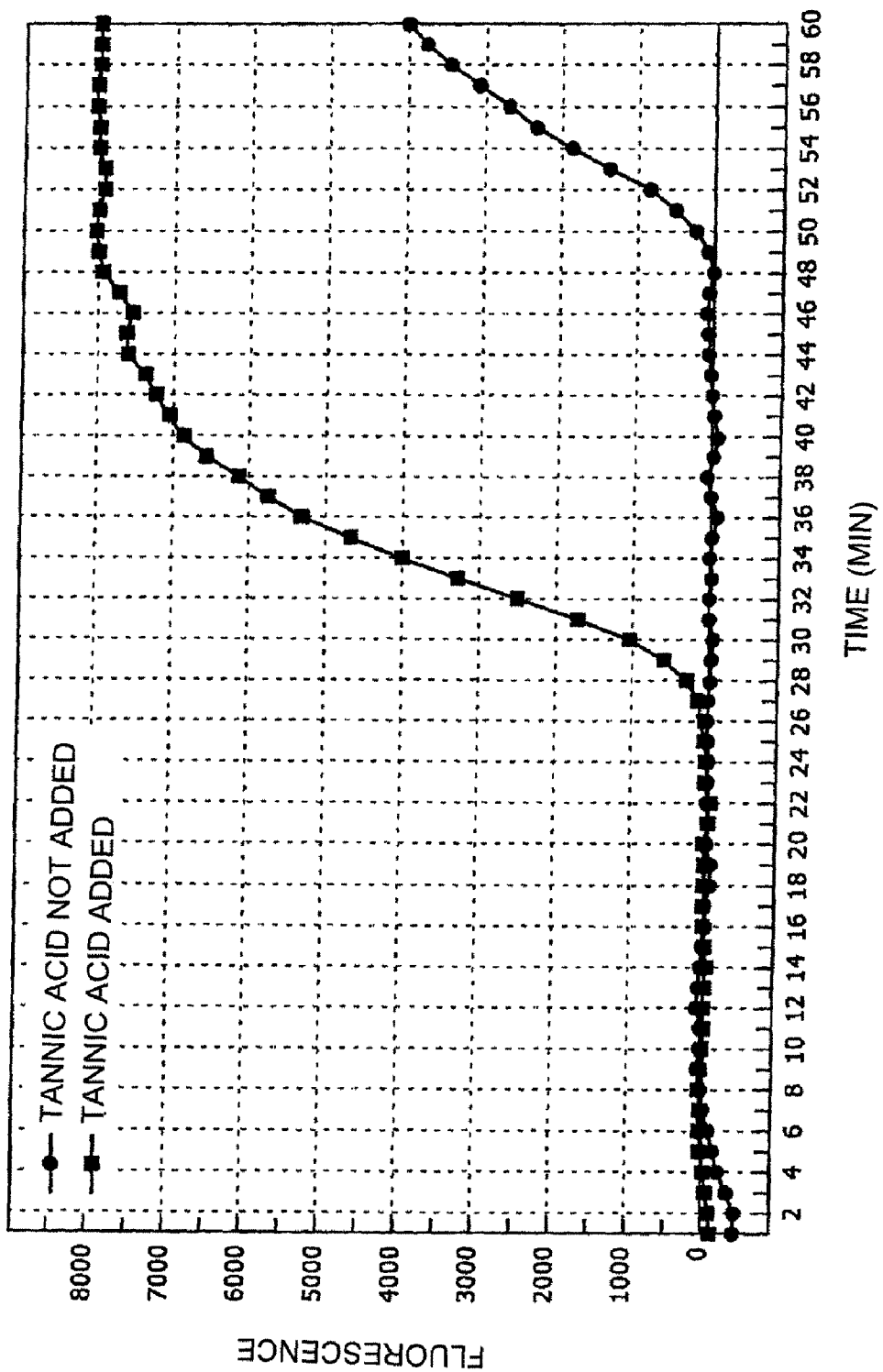
FIG. 3 is a graph showing results by the SMAP method in Example 1.
Figure 4:
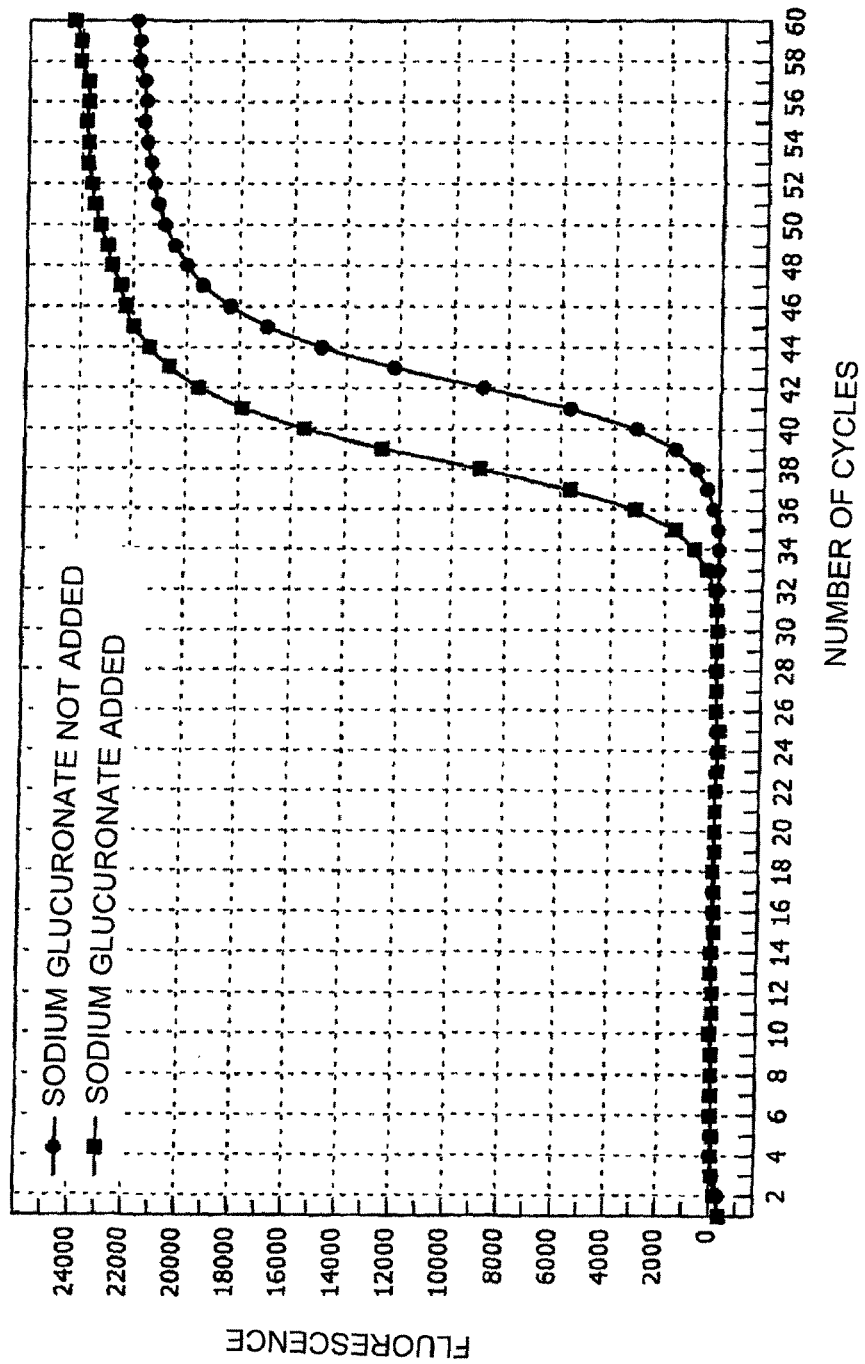
FIG. 4 is a graph showing results by the PCR method in Example 1.
Figure 6:
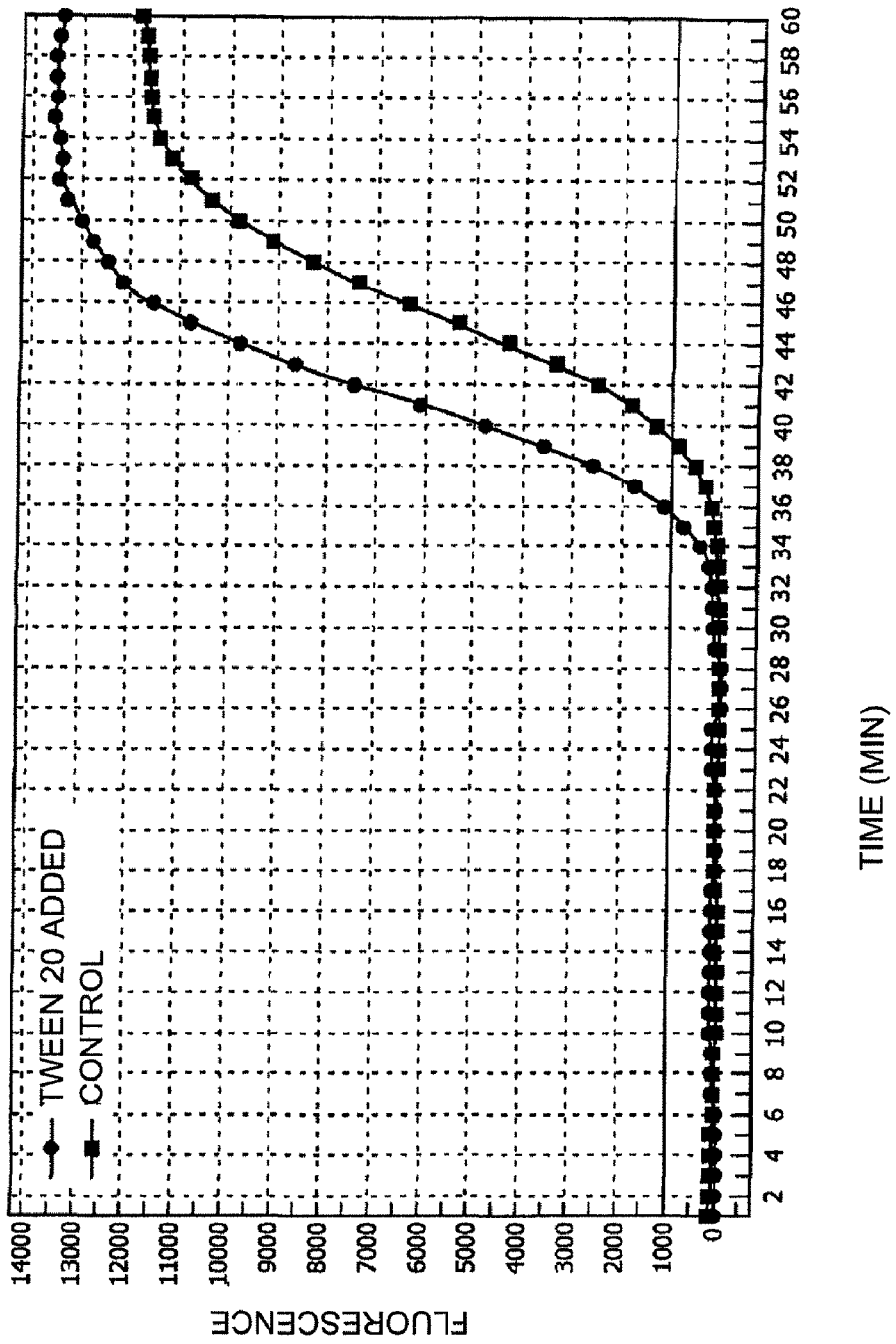
FIG. 6 is a graph showing results by the SMAP method in Example 2.
Figure 7:
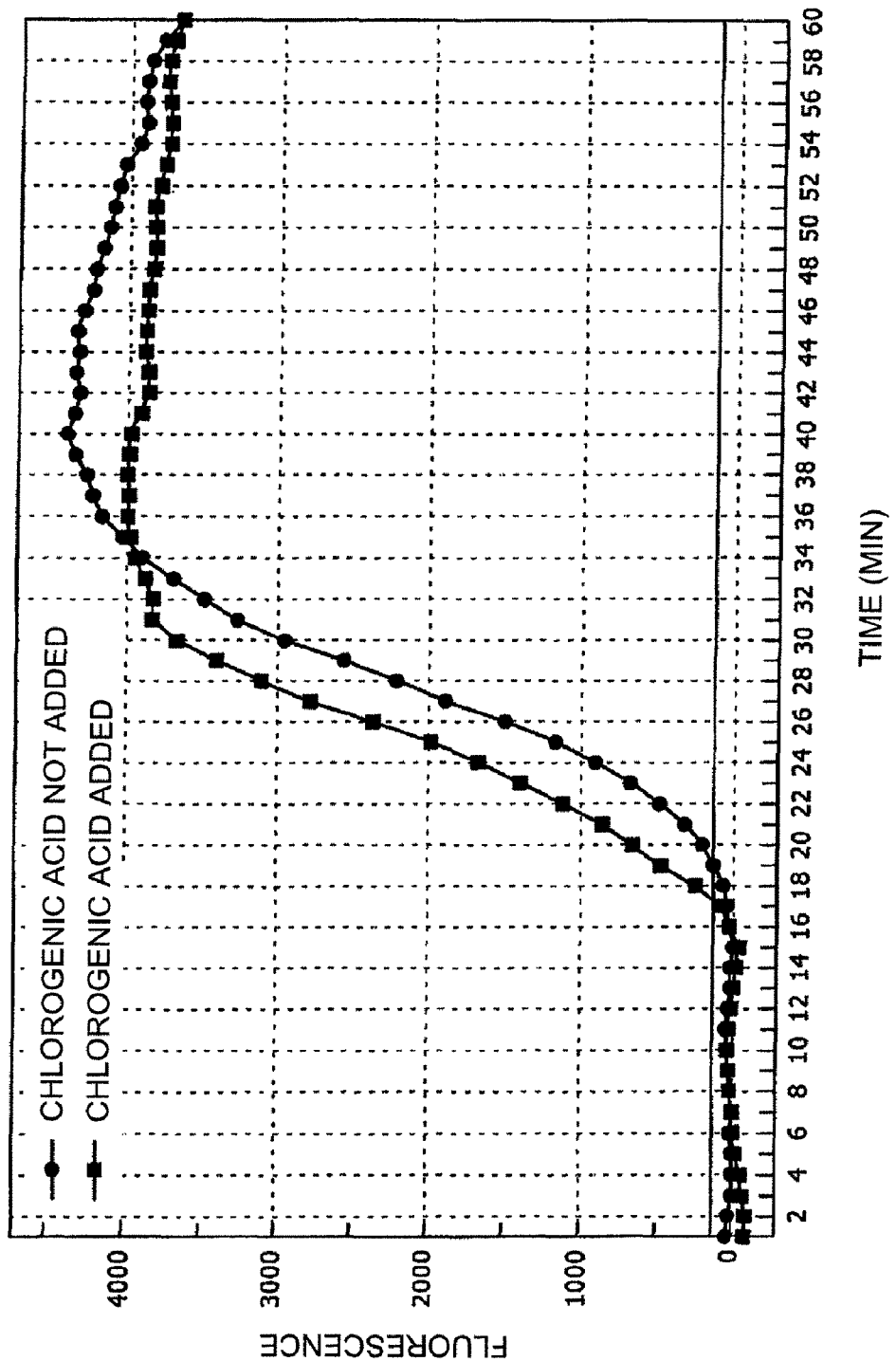
FIG. 7 is a graph showing results by the SMAP method in Example 3.
Figure 8:
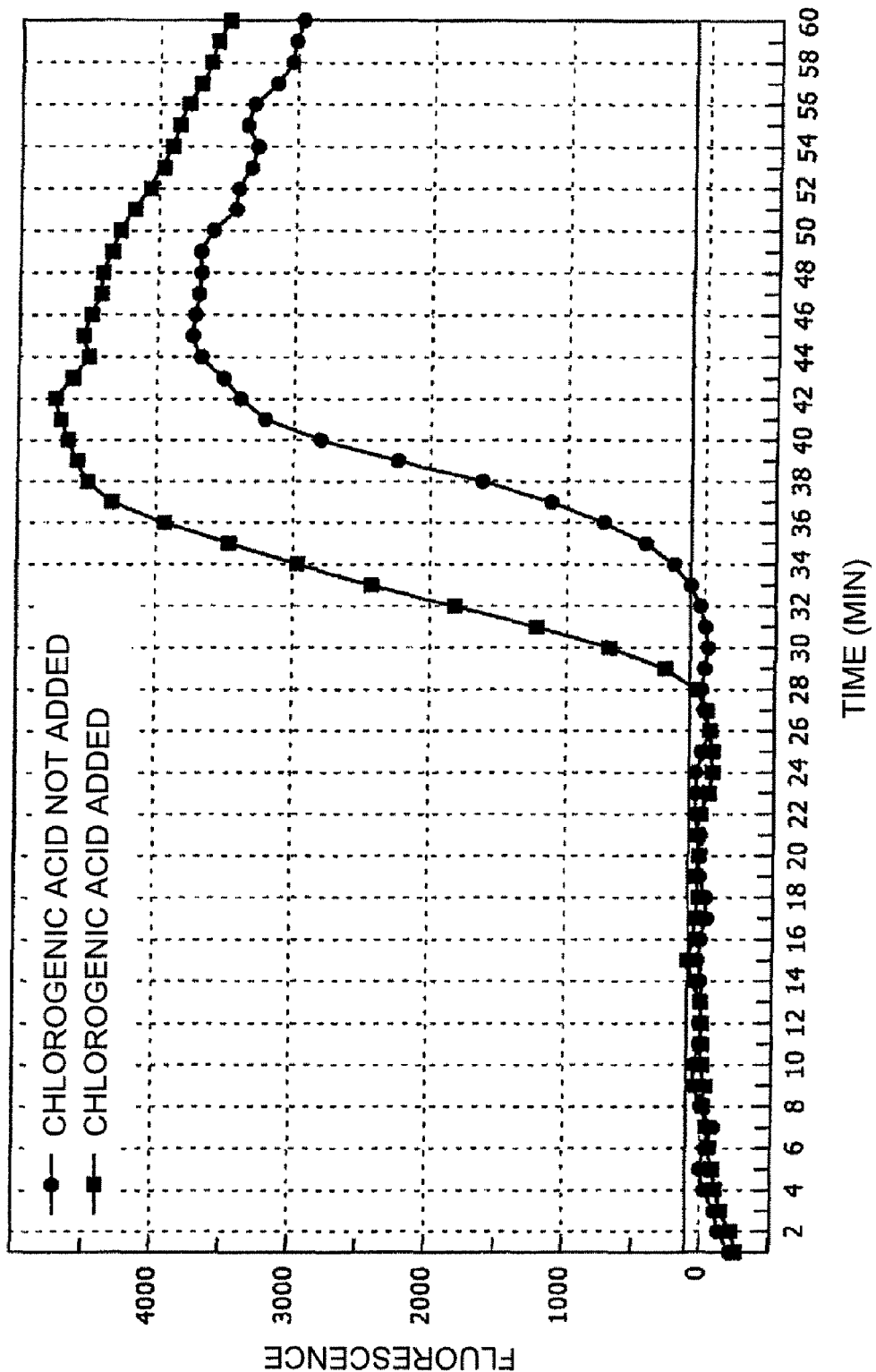
FIG. 8 is a graph showing results by the SMAP method in Example 4.
Figure 9:
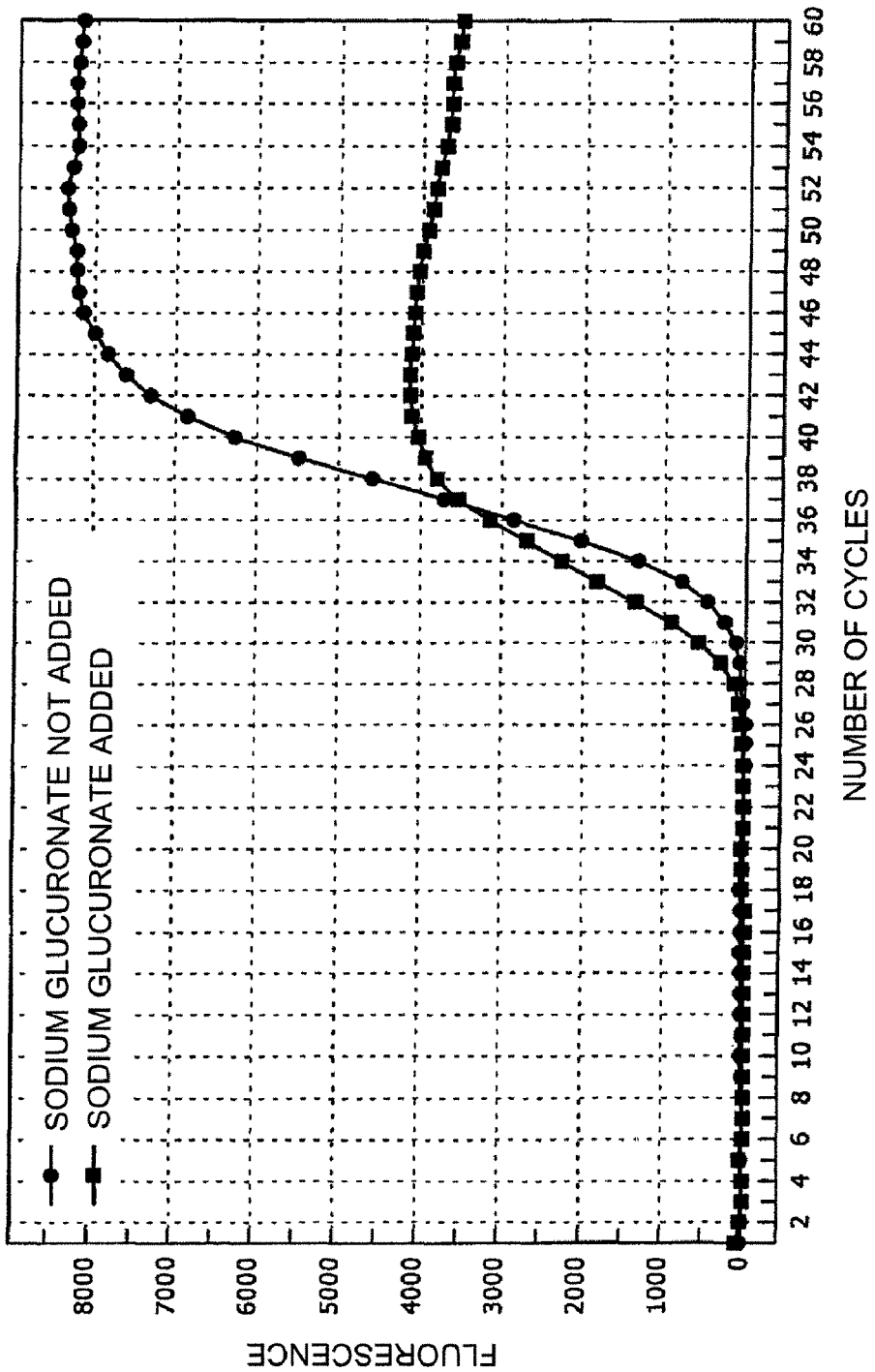
FIG. 9 is a graph showing results by the PCR method in Example 4.
Figure 10:
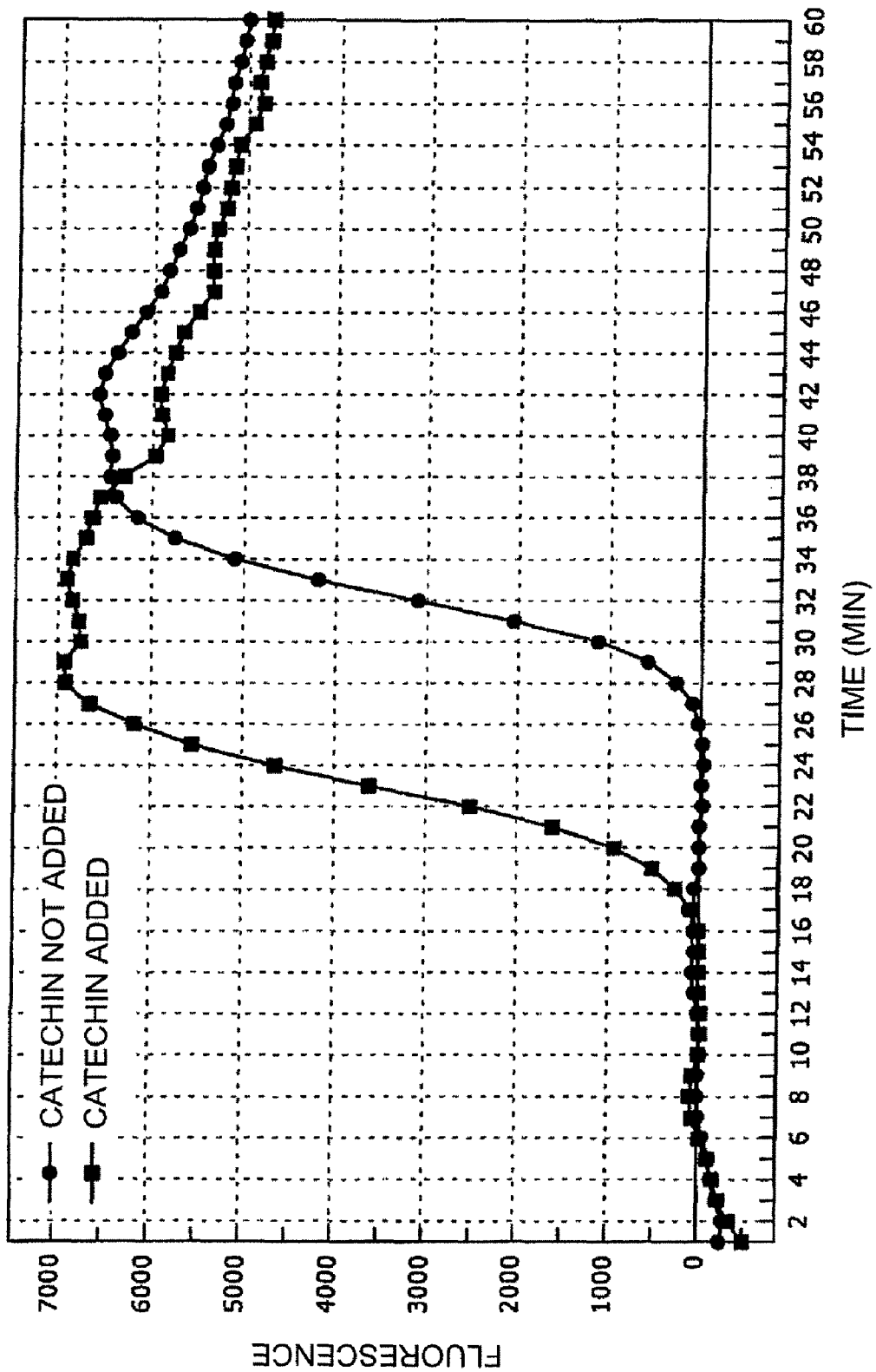
FIG. 10 is a graph showing results by the SMAP method in Example 5.
Figure 11:
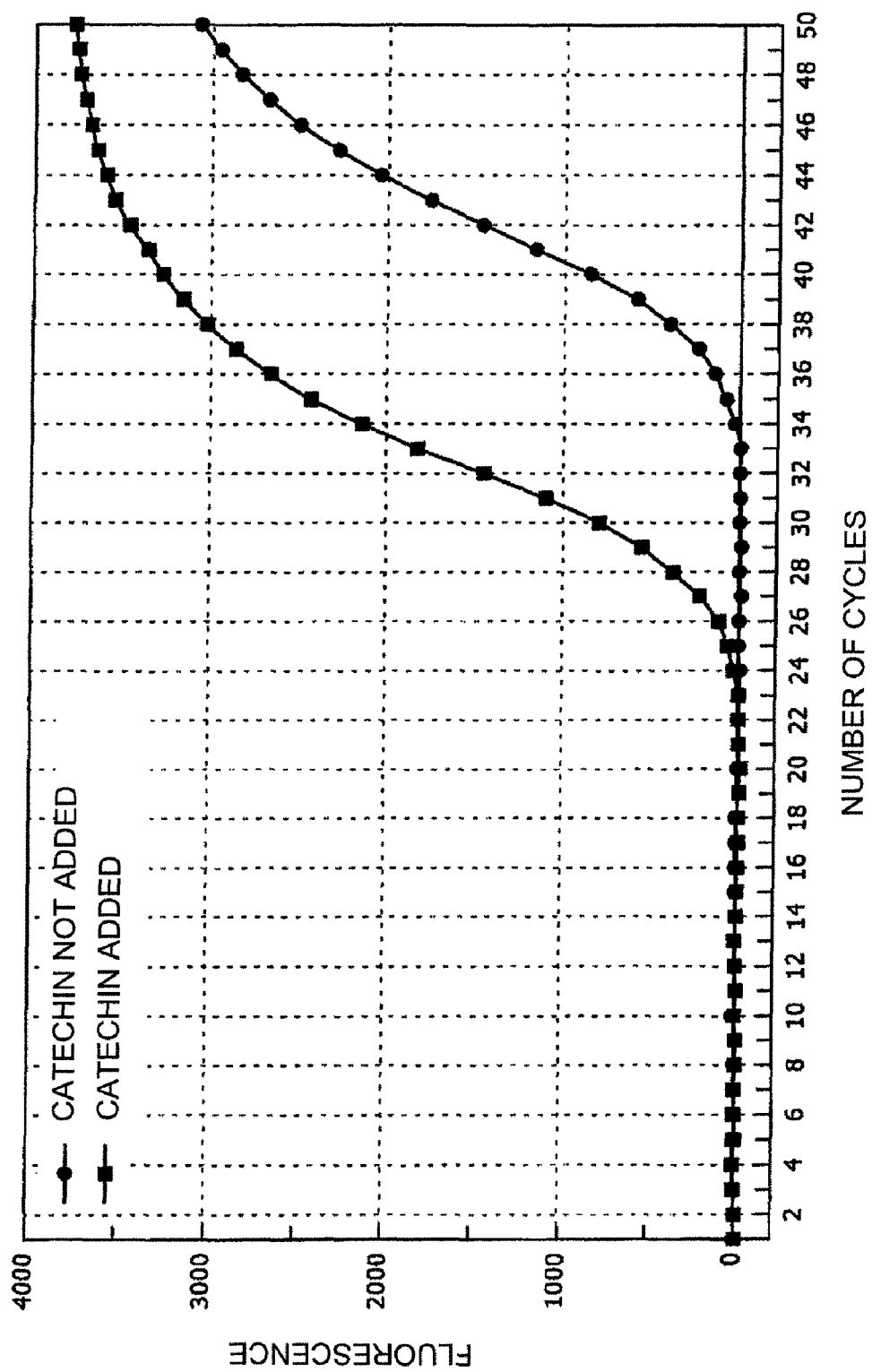
FIG. 11 is a graph showing results by the PCR method in Example 5.
Figure 12:
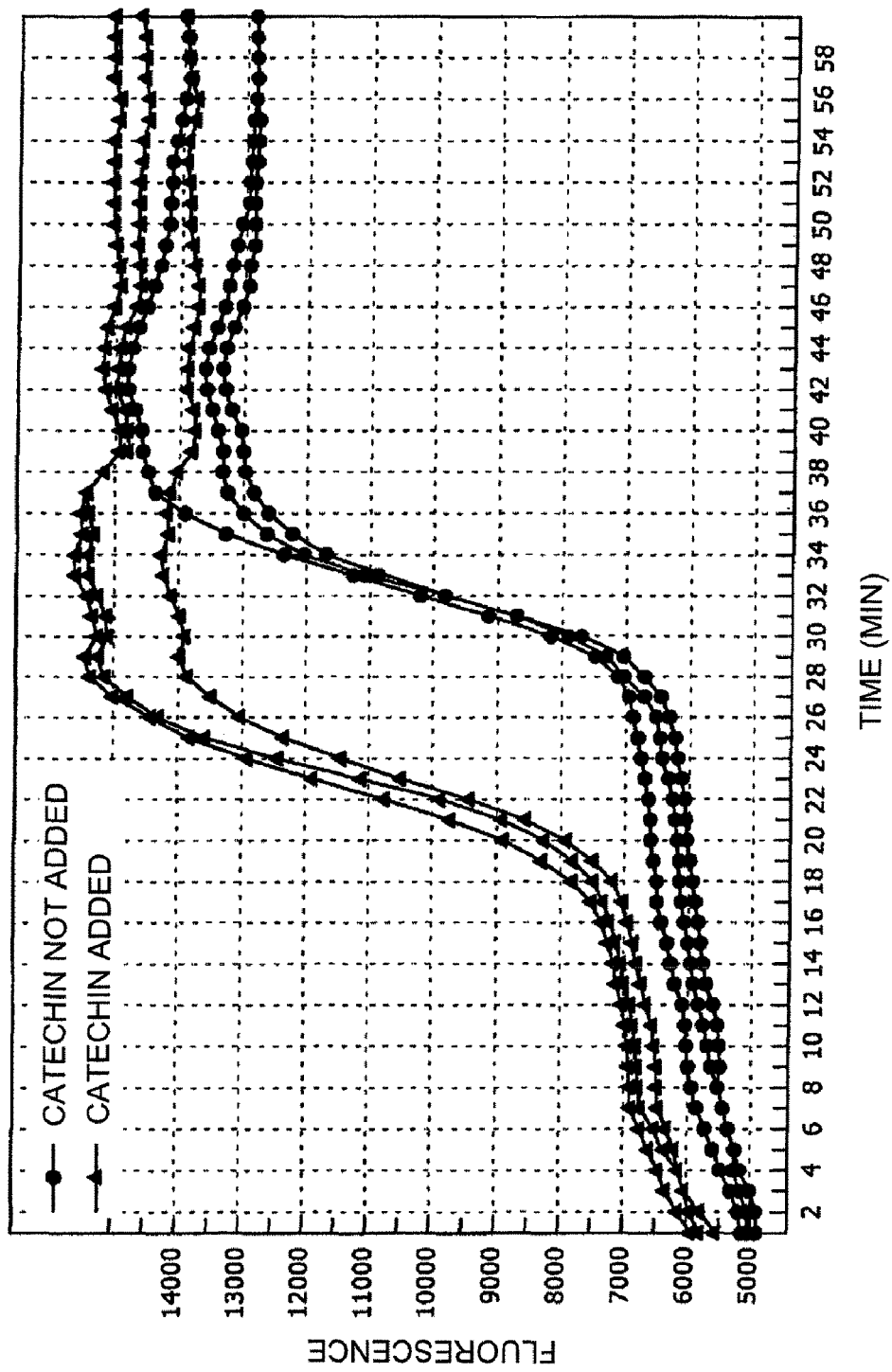
FIG. 12 is a graph showing results by the SMAP method in Example 6.
Figure 13:
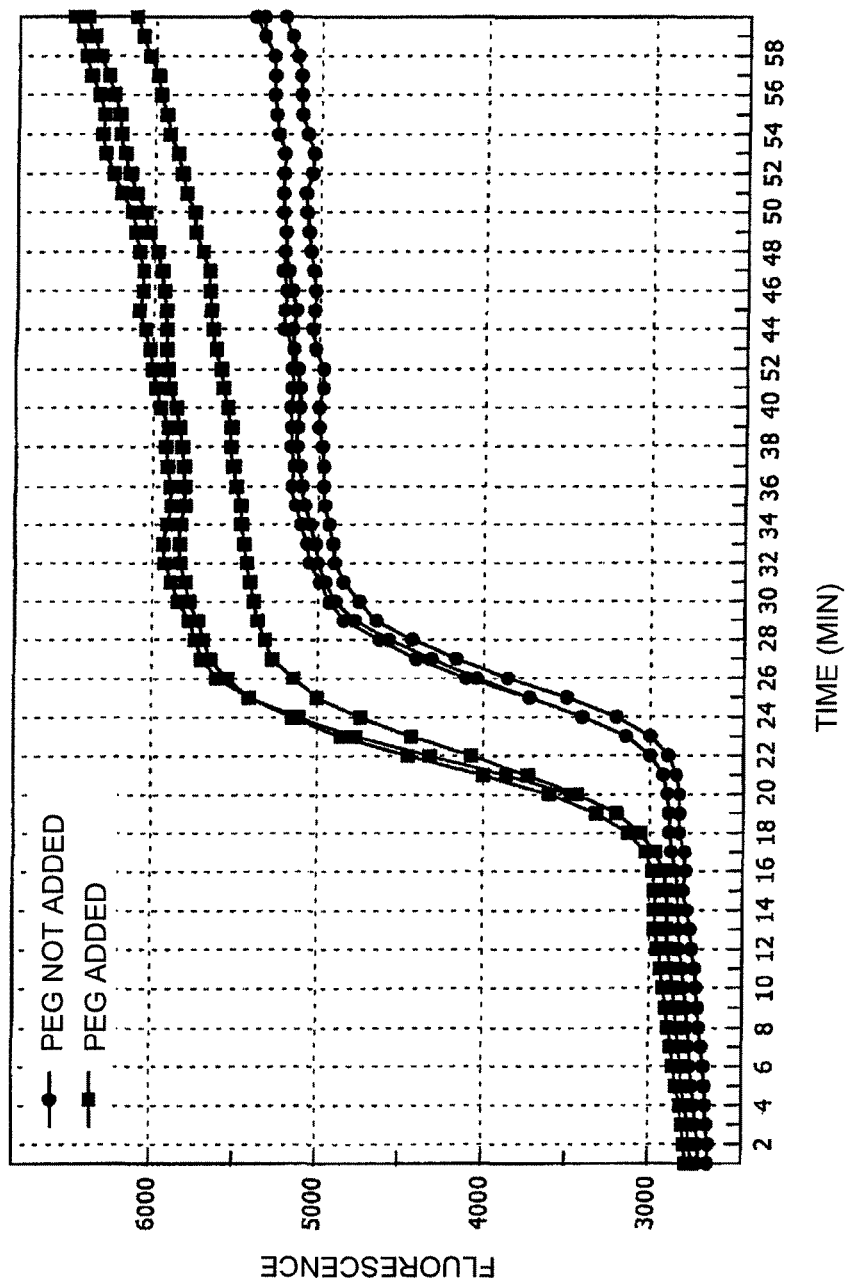
FIG. 13 is a graph showing results by the SMAP method in Example 6.
Figure 14:
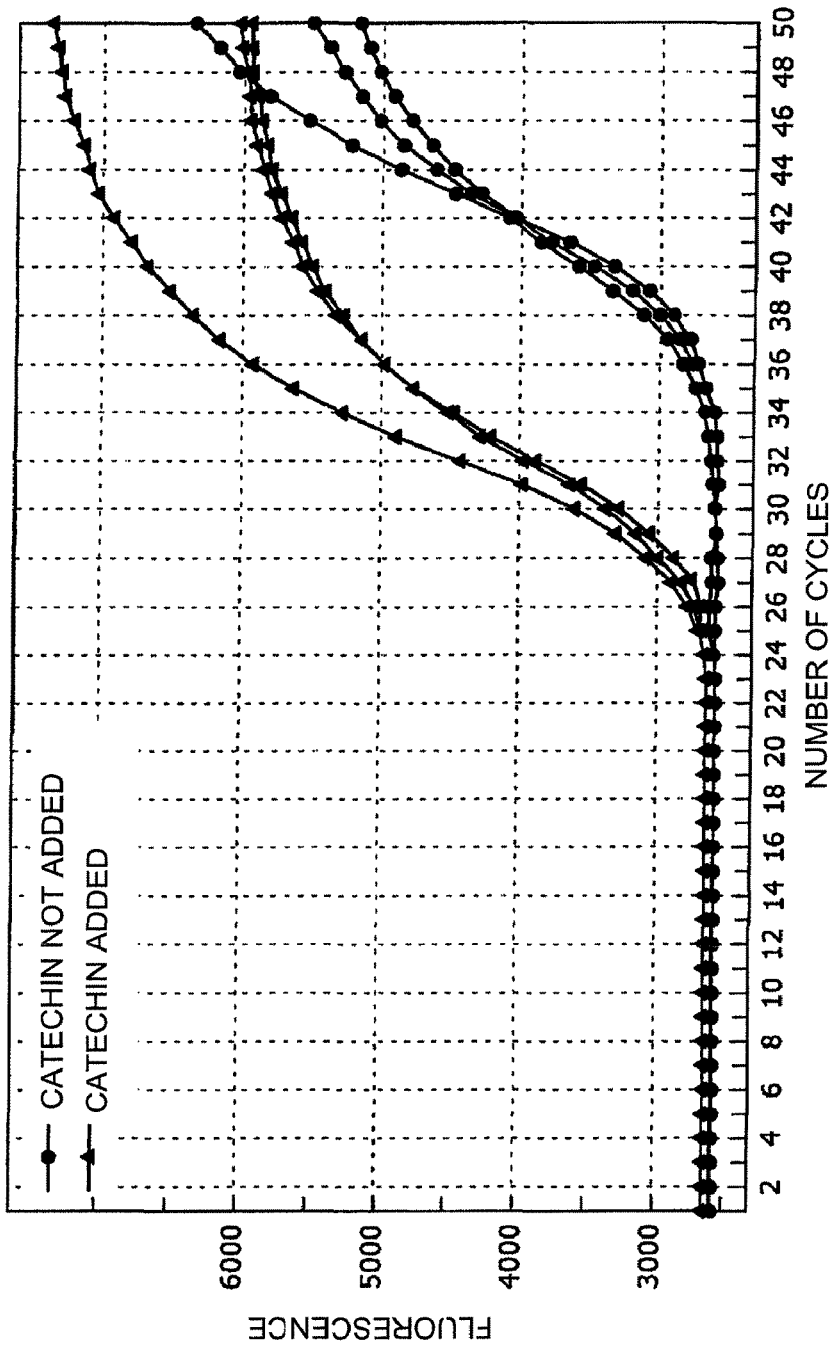
FIG. 14 is a graph showing results by the PCR method in Example 6.
Figure 15:
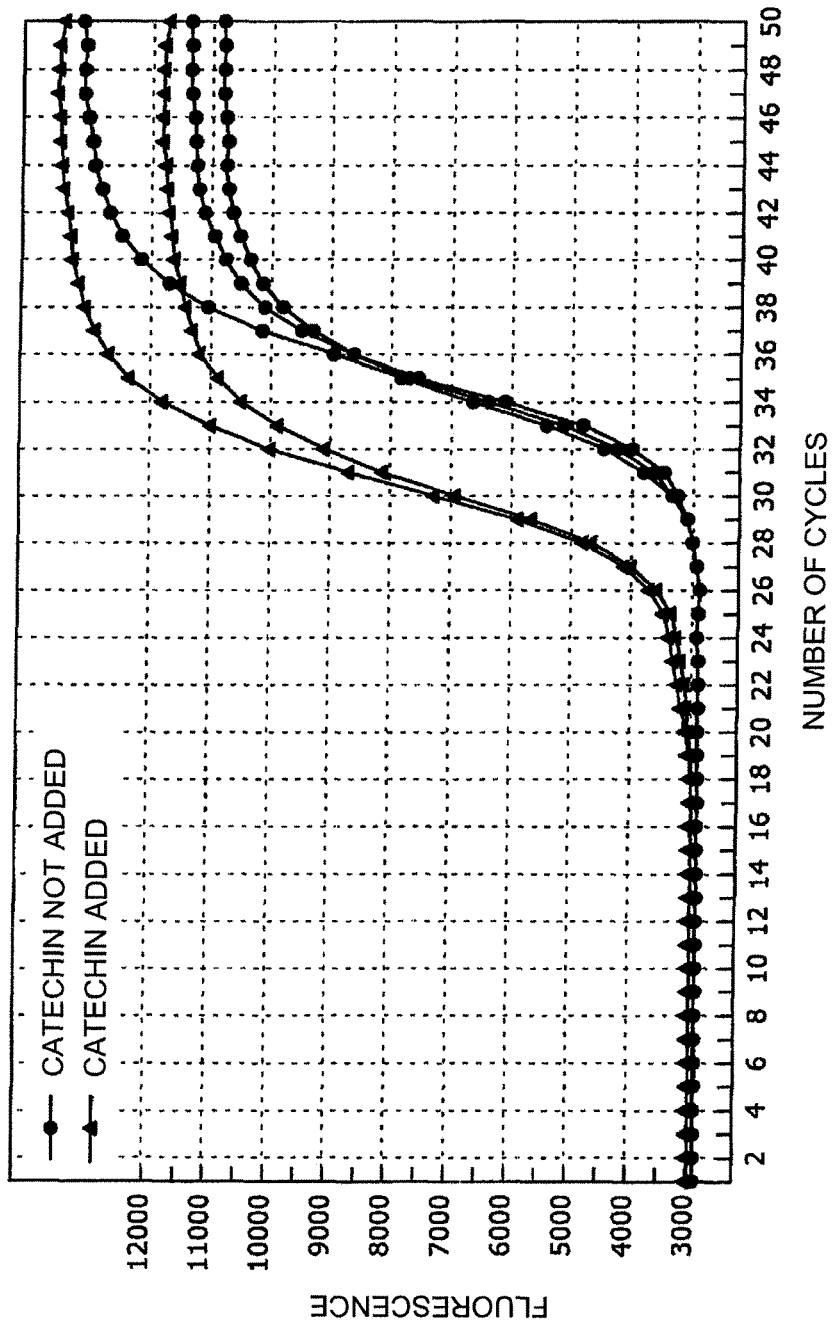
FIG. 15 is a graph showing results by the PCR method in Example 6.

```
<160> NUMBER OF SEQ ID NOS: 15

<210> SEQ ID NO 1
<211> LENGTH: 30
<212> TYPE: DNA
<213> ORGANISM: Artificial
<220> FEATURE:
<223> OTHER INFORMATION: forward primer 2D6*44-F1

<400> SEQUENCE: 1
cgctgcacat ggcctggggc ctcctgctca                              30

<210> SEQ ID NO 2
<211> LENGTH: 36
<212> TYPE: DNA
<213> ORGANISM: Artificial
<220> FEATURE:
<223> OTHER INFORMATION: reverse primer 2D6*44-SR2

<400> SEQUENCE: 2
```

-continued

```
tttatatata tataaacccc tgcactgttt cccaga                            36

<210> SEQ ID NO 3
<211> LENGTH: 122
<212> TYPE: DNA
<213> ORGANISM: Homo sapiens

<400> SEQUENCE: 3
cgggatggtg accacctcga ccacgctggc ctggggcctc ctgctcatga tcctacatcc   60
ggatgtgcag cgtgagccca tctgggaaac agtgcagggg ccgagggagg aagggtacag  120
gc                                                                 122

<210> SEQ ID NO 4
<211> LENGTH: 16
<212> TYPE: DNA
<213> ORGANISM: Artificial
<220> FEATURE:
<223> OTHER INFORMATION: loop primer 2D6*44-LF4

<400> SEQUENCE: 4
atccggatgt aggatc                                                  16

<210> SEQ ID NO 5
<211> LENGTH: 18
<212> TYPE: DNA
<213> ORGANISM: Artificial
<220> FEATURE:
<223> OTHER INFORMATION: 2D6*44OF4

<400> SEQUENCE: 5
gatggtgacc acctcgac                                                18

<210> SEQ ID NO 6
<211> LENGTH: 18
<212> TYPE: DNA
<213> ORGANISM: Artificial
<220> FEATURE:
<223> OTHER INFORMATION: 2D6*44OR4

<400> SEQUENCE: 6
tgtacccttc ctccctcg                                                18

<210> SEQ ID NO 7
<211> LENGTH: 20
<212> TYPE: DNA
<213> ORGANISM: Artificial
<220> FEATURE:
<223> OTHER INFORMATION: UCP1 PF1

<400> SEQUENCE: 7
cttgggtagt gacaaagtat                                              20

<210> SEQ ID NO 8
<211> LENGTH: 20
<212> TYPE: DNA
<213> ORGANISM: Artificial
<220> FEATURE:
<223> OTHER INFORMATION: UCP1 PR1

<400> SEQUENCE: 8
ccaaagggtc agatttctac                                              20

<210> SEQ ID NO 9
<211> LENGTH: 600
<212> TYPE: DNA
```

<213> ORGANISM: Homo sapiens

<400> SEQUENCE: 9

```
ataatattaa tgtaaatgta tattatatat aaatgttata gtaattataa cttgggtagt    60
gacaaagtat taatttatta ggtgaagtat atgcttttt  attagtgata ataaatatat   120
cctctctccc attataaaag tttgtatttc ttcttttaga aattgattct tctgtcattt   180
gcacatttat ctgtataatt ataacagggt atttcccagt ggtggctaat gagagaatta   240
tgggaaagta tagaacacta ttcaaatgca aagcactgta tgatttttat ttaataggaa   300
gacattttgt gcagcgattt ctgattgacc acagtttgat caagtgcatt tgttaatgtg   360
ttctacattt tcaaaaagga aaggagaatt tgttacattc agaacttgct gccactcctt   420
tgctacgtca taaagggtca gttgcccttg ctcatactga cctattcttt acctctctgc   480
ttcttctttg tgccagaaga gtagaaatct gacccttttgg ggataccacc ctctccccta   540
ctgctctctc caacctgagg caaactttct cctacttccc agagcctgtc agaagtggtg   600
```

<210> SEQ ID NO 10
<211> LENGTH: 163
<212> TYPE: DNA
<213> ORGANISM: Homo sapiens

<400> SEQUENCE: 10

```
tattaaatgc ttttaattta ataaattatt gttttctctt agatatgcaa taattttccc    60
actatcattg attatttccc gggaacccat aacaaattac ttaaaaacct tgcttttatg   120
gaaagtgata ttttggagaa agtaaaagaa caccaagaat cga                    163
```

<210> SEQ ID NO 11
<211> LENGTH: 41
<212> TYPE: DNA
<213> ORGANISM: Artificial
<220> FEATURE:
<223> OTHER INFORMATION: CYP2C19-2 FP

<400> SEQUENCE: 11

```
cctatatata taggaggt ttttaagtaa tttgttatgg g                         41
```

<210> SEQ ID NO 12
<211> LENGTH: 39
<212> TYPE: DNA
<213> ORGANISM: Artificial
<220> FEATURE:
<223> OTHER INFORMATION: CYP2C19-2 TP(W)

<400> SEQUENCE: 12

```
cccgggaaat aatcataaat tattgttttc tcttagata                           39
```

<210> SEQ ID NO 13
<211> LENGTH: 20
<212> TYPE: DNA
<213> ORGANISM: Artificial
<220> FEATURE:
<223> OTHER INFORMATION: CYP2C19-2 BP

<400> SEQUENCE: 13

```
tgatagtggg aaaattattg                                               20
```

<210> SEQ ID NO 14
<211> LENGTH: 18
<212> TYPE: DNA
<213> ORGANISM: Artificial
<220> FEATURE:

```
<223> OTHER INFORMATION: CYP2C19-2 OP1

<400> SEQUENCE: 14
tattaaatgc ttttaatt                                                    18

<210> SEQ ID NO 15
<211> LENGTH: 18
<212> TYPE: DNA
<213> ORGANISM: Artificial
<220> FEATURE:
<223> OTHER INFORMATION: CYP2C19-2 OP2

<400> SEQUENCE: 15
tcgattcttg gtgttctt                                                    18
```

The invention claimed is:

1. A method for detecting a nucleic acid contained in a sample, comprising the steps of:
adding at least one polyphenol to the sample, wherein the sample has not been subjected to nucleic acid extraction or purification,
complementarily binding an oligonucleotide complementary to a part of the nucleic acid sequence of a nucleic acid to be detected to the part of the nucleic acid sequence in the sample, and
detecting the nucleic acid to be detected.

2. The method according to claim 1, further comprising a heating step, prior to, at the same time as, or subsequent to the step of adding the at least one polyphenol.

3. The method according to claim 1, further comprising a step of adding an alkaline solution, prior to, at the same time as, or subsequent to the step of adding the at least one polyphenol.

4. The method according to claim 1, wherein the sample is blood or oral mucosal cells.

5. The method according to claim 1, wherein the step of complementarily binding the oligonucleotide is a step of annealing a primer to a part of the nucleic acid sequence.

6. The method according to claim 5, further comprising a step of amplifying a nucleic acid strand by elongating a nucleic acid from the 3' end of a primer after the step of annealing the primer to the part of the nucleic acid sequence.

7. The method according to claim 6, wherein the step of amplifying a nucleic acid strand is isothermal amplification.

8. The method according to claim 6, wherein the step of amplifying a nucleic acid strand is selected from the group consisting of PCR methods, the TMA method, the NASBA method, the LAMP method, the ICAN method, the RCA method, the SDA method, the TRC method, and the MITANI method.

9. The method according to claim 6, wherein the step of amplifying a nucleic acid is the LAMP method or the MITANI method.

10. The method according to claim 1, wherein the polyphenol is any of catechin, chlorogenic acid, tannic acid, flavonoid, tannin, rutin, quercetin, isoflavone, and anthocyanin or a mixture thereof.

11. A method for detecting and/or amplifying a nucleic acid contained in a sample, comprising the steps of:
adding at least one polyphenol to the sample, wherein the sample has not been subjected to nucleic acid extraction or purification,
complementarily binding an oligonucleotide complementary to a part of the nucleic acid sequence of a nucleic acid to be detected to the part of the nucleic acid sequence in the sample,
amplifying the nucleic acid by an isothermal amplification method, and
detecting the nucleic acid to be detected,
wherein the polyphenol is any of catechin, chlorogenic acid, tannic acid, flavonoid, tannin, rutin, quercetin, isoflavone, and anthocyanin or a mixture thereof.

* * * * *